US012599489B2

(12) United States Patent
 Ahn

(10) Patent No.: US 12,599,489 B2
(45) Date of Patent: Apr. 14, 2026

(54) SPINAL CAGE FIXABLE THROUGH INSERTION OF BONE SCREWS

(71) Applicants: GBS Commonwealth Co., Ltd., Seoul (KR); PMT Republic, Inc., Walnut, CA (US)

(72) Inventor: Kyoung Gee Ahn, Seoul (KR)

(73) Assignees: GBS Commonwealth Co., Ltd., Seoul (KR); PMT Republic, Inc., Walnut, CA (US)

( * ) Notice: Subject to any disclaimer, the term of this patent is extended or adjusted under 35 U.S.C. 154(b) by 4 days.

(21) Appl. No.: 18/795,173

(22) Filed: Aug. 5, 2024

(65) Prior Publication Data

US 2025/0387237 A1 Dec. 25, 2025

(30) Foreign Application Priority Data

Jun. 20, 2024 (KR) ........................ 10-2024-0080011

(51) Int. Cl.
 *A61F 2/44* (2006.01)
 *A61F 2/30* (2006.01)

(52) U.S. Cl.
 CPC .... *A61F 2/447* (2013.01); *A61F 2002/30433* (2013.01); *A61F 2002/30774* (2013.01)

(58) Field of Classification Search
 CPC ....... A61F 2/4455–447; A61B 17/8038; A61B 17/8047; A61B 17/8052
 See application file for complete search history.

(56) References Cited

U.S. PATENT DOCUMENTS

| | | | | | |
|---|---|---|---|---|---|
| 7,163,561 | B2 * | 1/2007 | Michelson | ............ | A61F 2/4455 623/908 |
| 7,850,731 | B2 * | 12/2010 | Brittan | .................. | A61F 2/4611 623/17.11 |
| 2002/0193880 | A1 * | 12/2002 | Fraser | ................... | A61F 2/4465 623/17.11 |
| 2009/0105831 | A1 * | 4/2009 | Jones | ................. | A61B 17/7059 606/301 |
| 2009/0234455 | A1 * | 9/2009 | Moskowitz | ........ | A61B 17/0642 606/301 |
| 2010/0070037 | A1 * | 3/2010 | Parry | ................. | A61B 17/8085 623/17.16 |

(Continued)

FOREIGN PATENT DOCUMENTS

CN 213250069 U 5/2021

*Primary Examiner* — Eduardo C Robert
*Assistant Examiner* — Anna V. Little
(74) *Attorney, Agent, or Firm* — NKL Law; Jae Youn Kim

(57) ABSTRACT

Disclosed is a spinal cage fixable through insertion of bone screws including a cage body, a receiver disposed on a front surface of the cage body and provided with a plurality of screw holes formed therein so that the bone screws pass through the screw holes to be inserted thereinto, and a fixture coupled to the receiver adjacent to the screw holes and configured to selectively block a portion of each screw hole, wherein, when each bone screw enters a corresponding screw hole, a front end of the fixture is moved in an outward direction of the corresponding screw hole, and when insertion of each bone screw into the corresponding screw hole has been completed, the front end of the fixture is moved in an inward direction of the corresponding screw hole to prevent each bone screw from being separated from the corresponding screw hole.

8 Claims, 18 Drawing Sheets

(56)          References Cited

U.S. PATENT DOCUMENTS

| | | | |
|---|---|---|---|
| 2014/0005727 A1* | 1/2014 | Kraemer | A61F 2/4455 |
| | | | 606/279 |
| 2014/0277456 A1* | 9/2014 | Kirschman | A61F 2/447 |
| | | | 623/17.11 |
| 2015/0209089 A1* | 7/2015 | Chataigner | A61F 2/4611 |
| | | | 623/17.16 |
| 2017/0071750 A1* | 3/2017 | Urban | A61F 2/4611 |
| 2017/0181781 A1* | 6/2017 | Dubois | A61B 17/80 |
| 2018/0303622 A1 | 10/2018 | Laurence et al. | |
| 2020/0155325 A1* | 5/2020 | Suh | A61B 17/8052 |
| 2021/0059834 A1* | 3/2021 | Miguel | A61F 2/30749 |

* cited by examiner

SPINAL CAGE FIXABLE THROUGH INSERTION OF BONE SCREWS

CROSS-REFERENCE TO RELATED APPLICATIONS

This instant application claims priority to Korean Patent Application No. 10-2024-0080011, filed on Jun. 20, 2024, the disclosure of which is incorporated herein by reference in its entirety.

BACKGROUND OF THE INVENTION

Field of the Invention

The present invention relates to a spinal cage, and more particularly, to a spinal cage fixable through insertion of bone screws.

Description of the Related Art

The spine may have structural problems, such as a problem in stable alignment or narrowing of a distance between vertebral bodies, for congenital or degenerative reasons, or other reasons, such as accidents.

Representative spinal diseases include spinal deformities, spinal fractures, spinal disc herniation, spinal stenosis, posterior joint hypertrophy, etc., and these spinal diseases require surgical treatment when symptoms worsen and conservative treatment becomes difficult.

Among surgical treatment methods, spinal fusion is a procedure in which an intervertebral disc in which a spinal disease occurred is removed and then a spinal cage is inserted between vertebral bodies to secure a space into which the bone grows and enters for fusion, increase a distance between the vertebral bodies to reduce pain, and restore lordosis of the spine to maintain stability of the spine.

The spinal cage may increase the structural stability of the spine while maintaining a space between the vertebrae, may promote fusion of the vertebrae by filling the inside of the spinal cage with a material for bone grafting, may help to reduce the rehabilitation period of a patient after surgery and speed up recovery of the patient, and may maintain the distance between the vertebrae to reduce nerve compression and maintain an appropriate height of a disc space.

Various types of spinal cages have been developed depending on the surgical method or the like, and shapes of spinal cages to restore biomechanical stability of the spine while being implantable into the human body are being developed in various ways.

Since spinal cages must maintain a constant distance between the vertebral bodies, they has a solid structure formed of a metal material, such as titanium or a titanium alloy having mechanical properties suitable for supporting the load of the human body.

However, the conventional spinal cages have the risk of protruding from the vertebral bodies or deviating from the inserted position due to bending of the spine or force by the load after the spinal fusion procedure was completed.

Further, the conventional spinal cages have a large number of parts, require complicated parts, and thus make it difficult to assemble, require a lot of time to fix the spinal cage between the vertebral bodies, and increase the unit cost of a product due to the large number of parts.

Furthermore, the conventional spinal cages require bone screws to be fixed to a metal plate to maintain durability, and thus increase the risk of occurrence of tissue necrosis or the like due to the metal plate, and increase a surgical time.

The matters described above as background technology are only for enhancement of understanding of the background of the invention, and should not be taken as recognition that they correspond to prior art already known to those skilled in the art.

SUMMARY OF THE INVENTION

Therefore, the present invention has been made in view of the above problems, and it is an object of the present invention to provide a spinal cage fixable through insertion of bone screws that may be fixed between vertebrae by directly inserting the bone screws into a cage body.

It is another object of the present invention to provide a spinal cage fixable through insertion of bone screws that may cause a fixture to prevent the bone screws from being separated from a receiver after insertion of the bone screws into the receiver has been completed.

The objects of the present invention are not limited to the above-mentioned objects, and other objects not mentioned herein will be clearly understood by those skilled in the art from the following description.

In accordance with the present invention, the above and other objects can be accomplished by the provision of a spinal cage fixable through insertion of bone screws including a cage body, a receiver disposed on a front surface of the cage body and provided with a plurality of screw holes formed therein so that the bone screws pass through the screw holes to be inserted thereinto, and a fixture coupled to the receiver adjacent to the screw holes and configured to selectively block a portion of each screw hole, wherein, when each bone screw enters a corresponding screw hole, a front end of the fixture is moved in an outward direction of the corresponding screw hole, and when insertion of each bone screw into the corresponding screw hole has been completed, the front end of the fixture is moved in an inward direction of the corresponding screw hole to prevent each bone screw from being separated from the corresponding screw hole.

The receiver may include a receiving body disposed in front of the cage body, an upper protrusion configured to protrude upward from an upper surface of the receiving body and provided with the screw hole formed therein, and a lower protrusion configured to protrude downward from a lower surface of the receiving body and provided with the screw hole formed therein.

A rear surface of the upper protrusion may be formed as an inclined surface having a predetermined inclination angle with respect to a front surface of the upper protrusion so that a width of the upper protrusion in forward and rearward directions gradually decreases toward an upper end of the upper protrusion, and a rear surface of the lower protrusion may be formed as an inclined surface having the predetermined inclination angle with respect to a front surface of the lower protrusion so that a width of the lower protrusion in the forward and rearward directions gradually decreases toward a lower end of the lower protrusion.

A vertical height of the upper protrusion and the lower protrusion may be 1 mm to 15 mm.

An inclination angle of the rear surfaces of the upper protrusion and the lower protrusion may be 1° to 60°.

The fixture may include a support longitudinally coupled to an inside of the receiver, an extension configured to extend forward from a front surface of the support and be orthogonal to the support, and an upper and lower restraint part configured to extend from a front end of the extension to have a predetermined upward inclination angle and a predetermined downward inclination angle.

When each bone screw enters the corresponding screw hole, the extension may be deformed up or down and the upper and lower restraint part may be moved in the outward direction of the corresponding screw hole, and when insertion of each bone screw into the corresponding screw hole has been completed, the extension may return to an original form thereof and the upper and lower restraint part may be moved in the inward direction of the corresponding screw hole.

Among the bone screws formed in the receiver, the bone screw configured to enter the screw hole disposed in an upper area and the bone screw configured to enter the screw hole disposed in a lower area may not be capable of entering at the same time and may be capable of entering sequentially.

The upper and lower restraint part may prevent both the bone screw, insertion of which into the screw hole disposed in an upper area has been completed, and the bone screw, insertion of which into the screw hole disposed in a lower area has been completed, among the bone screws formed in the receiver, from being separated from the screw holes.

The fixture may include a support longitudinally coupled to an inside of the receiver, a first extension configured to extend forward from an upper portion of a front surface of the support and be orthogonal to the support, a second extension configured to extend forward from a lower portion of the front surface of the support and be orthogonal to the support, an upper restraint part configured to extend from a front end of the first extension to have a predetermined upward inclination angle, and a lower restraint part configured to extend from a front end of the second extension to have a predetermined downward inclination angle.

The upper restraint part may prevent the bone screw, insertion of which into the screw hole disposed in an upper area has been completed, among the bone screws formed in the receiver, from being separated from the screw hole disposed in the upper area, and the lower restraint part may prevent the bone screw, insertion of which into the screw hole disposed in a lower area has been completed, among the bone screws formed in the receiver, from being separated from the screw hole disposed in the lower area.

The fixture may include a support longitudinally coupled to an inside of the receiver, an extended inclined part configured to extend forward from a front portion of the support to have a predetermined inclination angle with respect to the support, and an orthogonal restraint part configured to extend orthogonally to a front end of the extended inclined part.

BRIEF DESCRIPTION OF THE DRAWINGS

The above and other objects, features and other advantages of the present invention will be more clearly understood from the following detailed description taken in conjunction with the accompanying drawings, in which.

4

Figure 3:
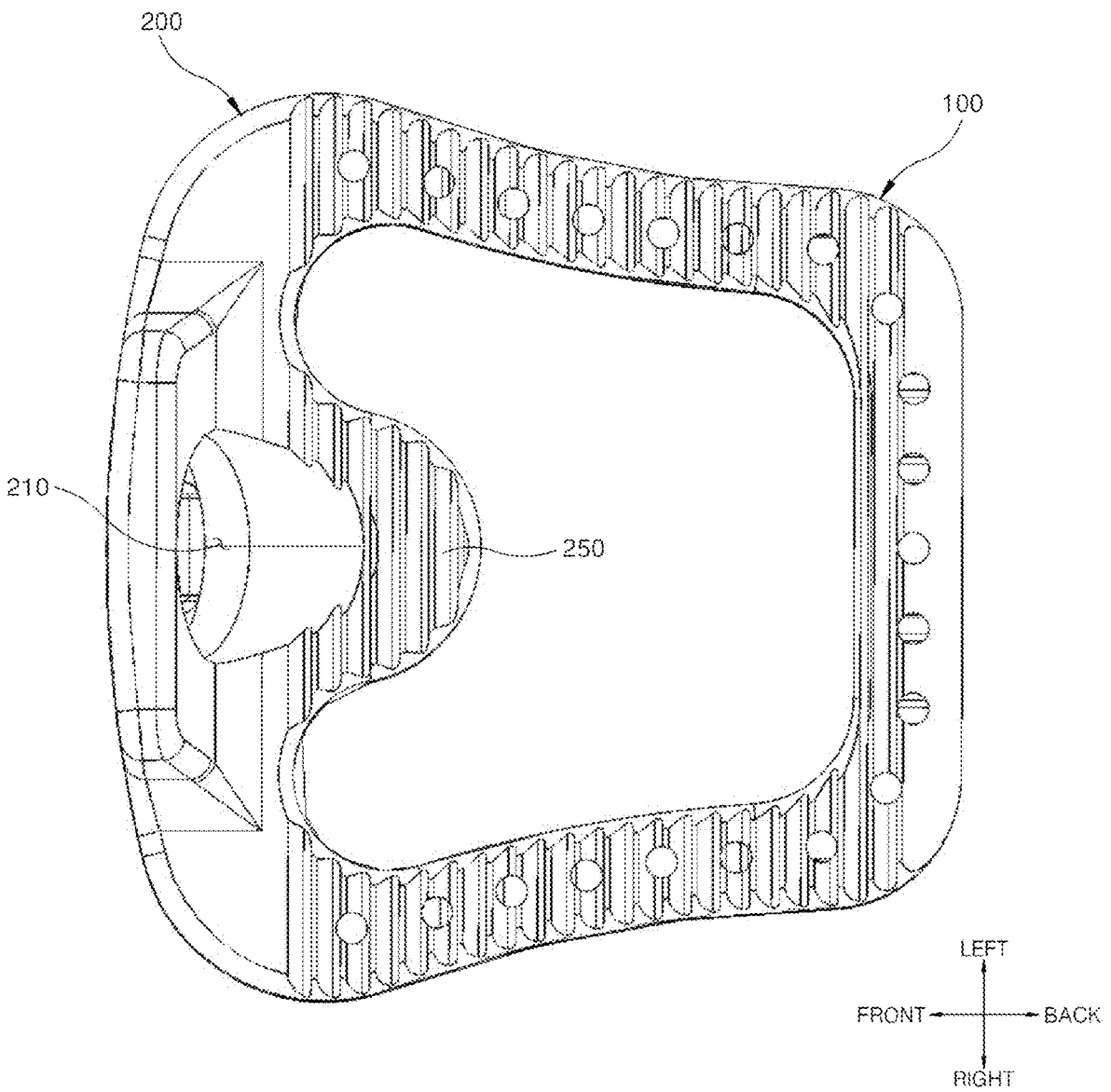
Figure 4:
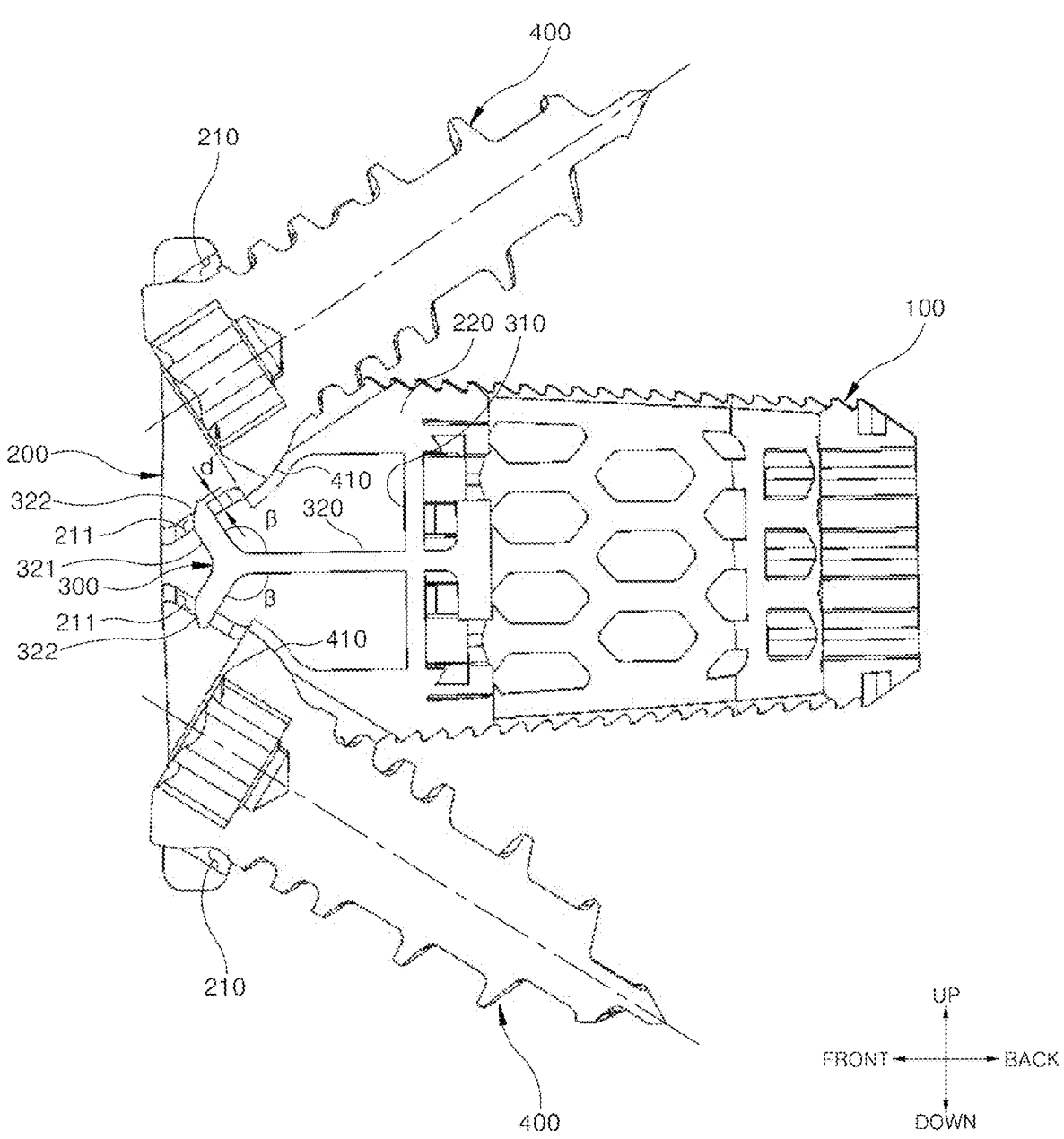
Figure 5:
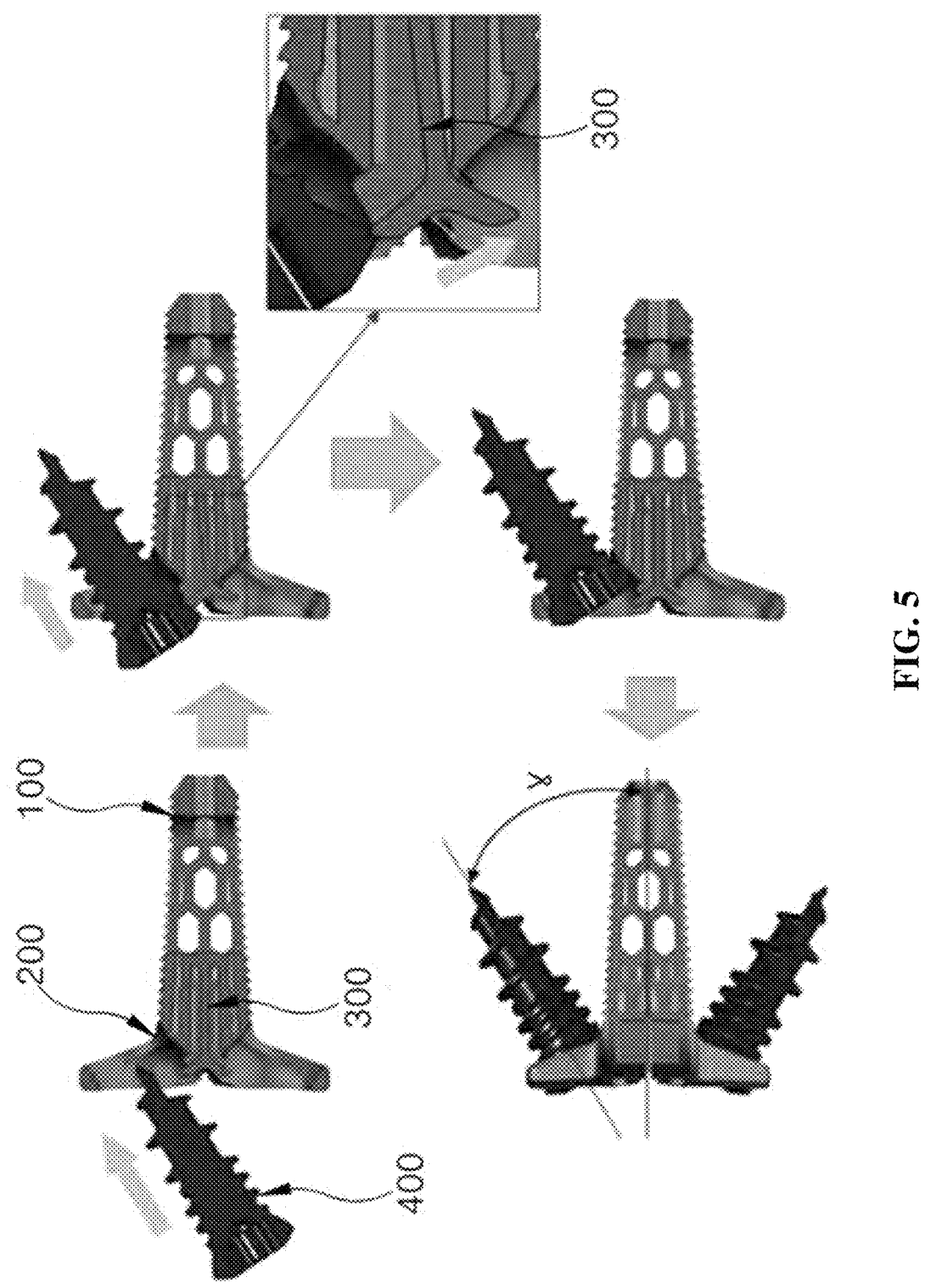
Figure 6:
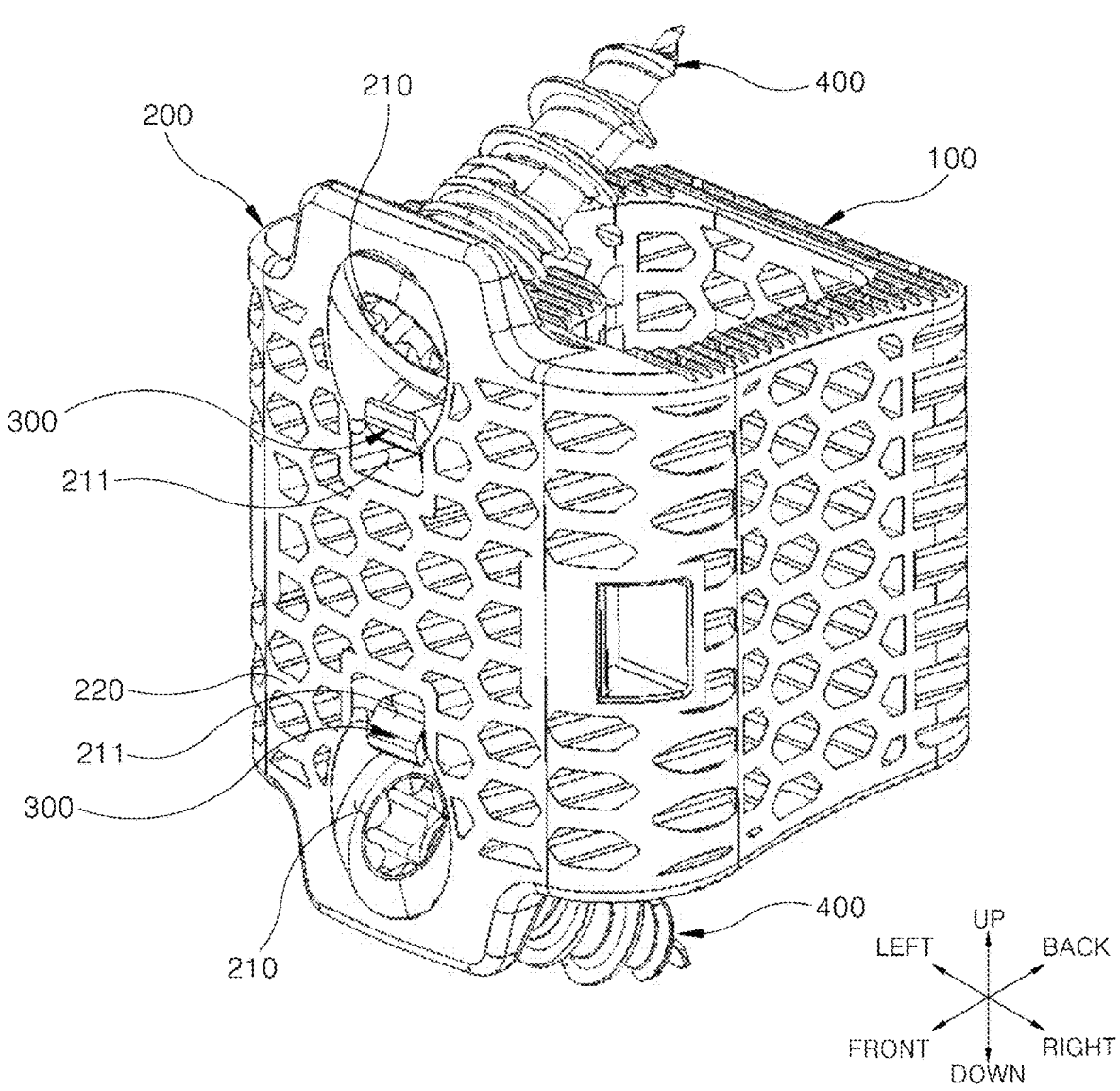
Figure 7:
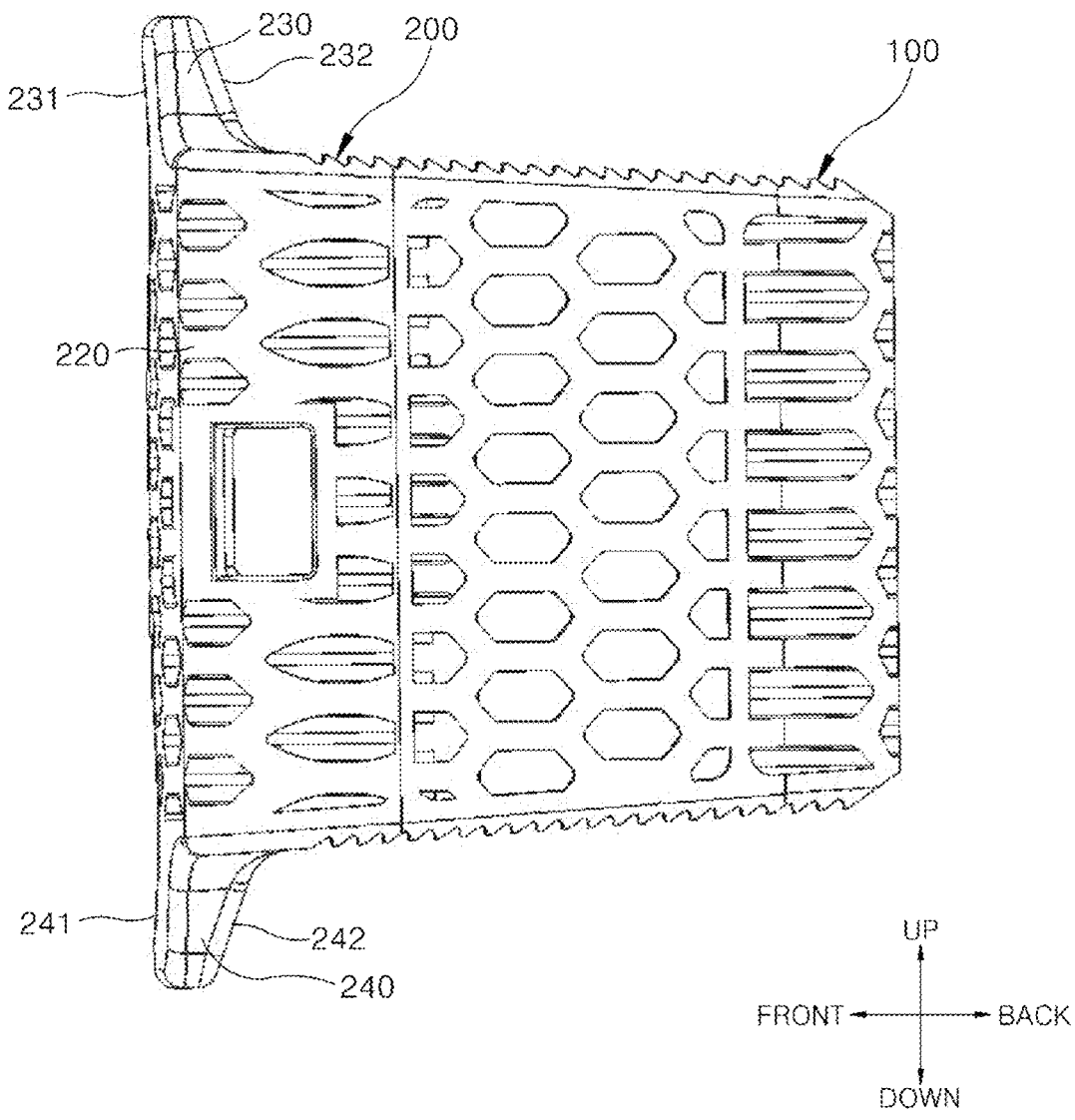
Figure 8:
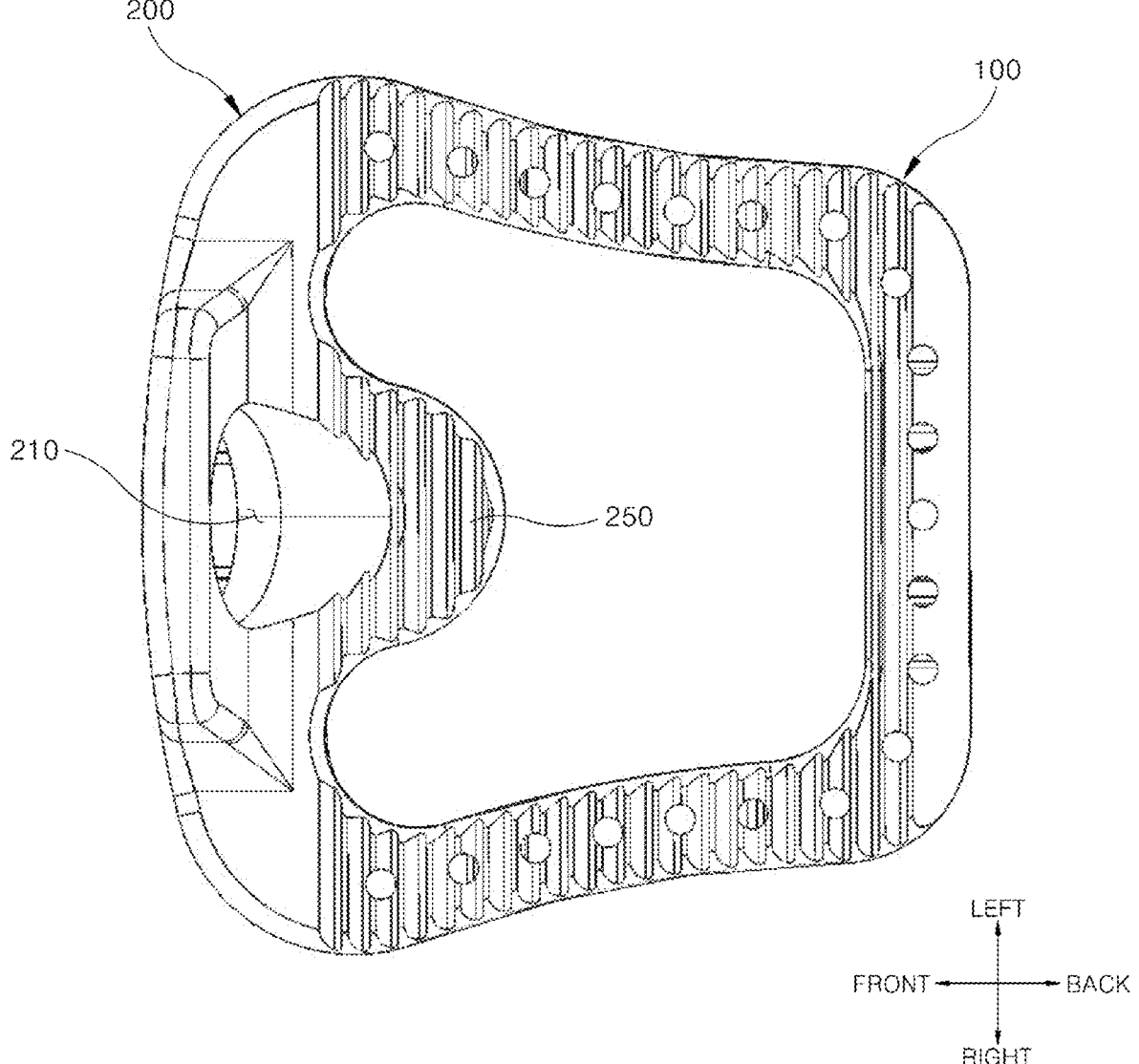
Figure 9:
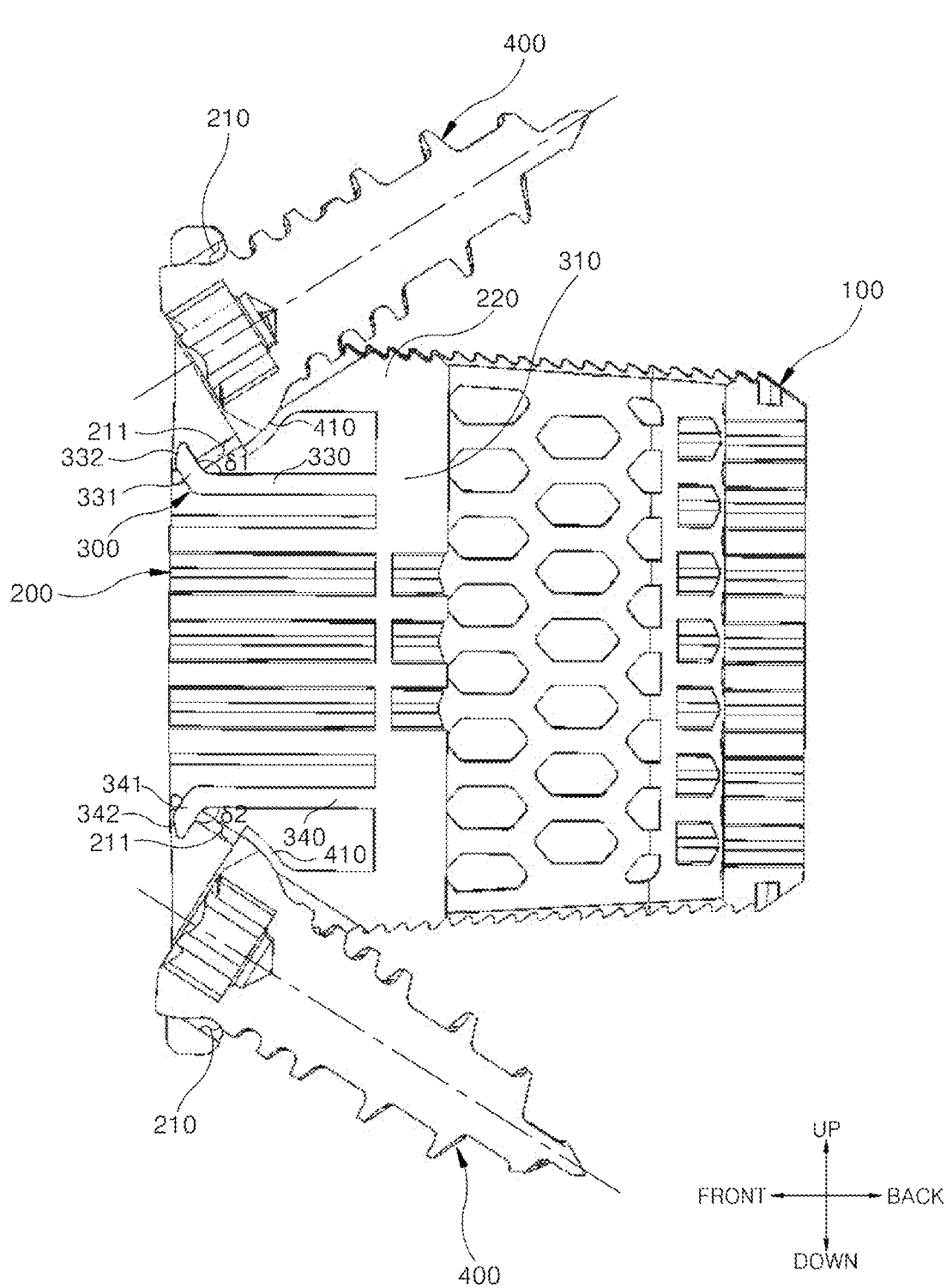
Figure 10:
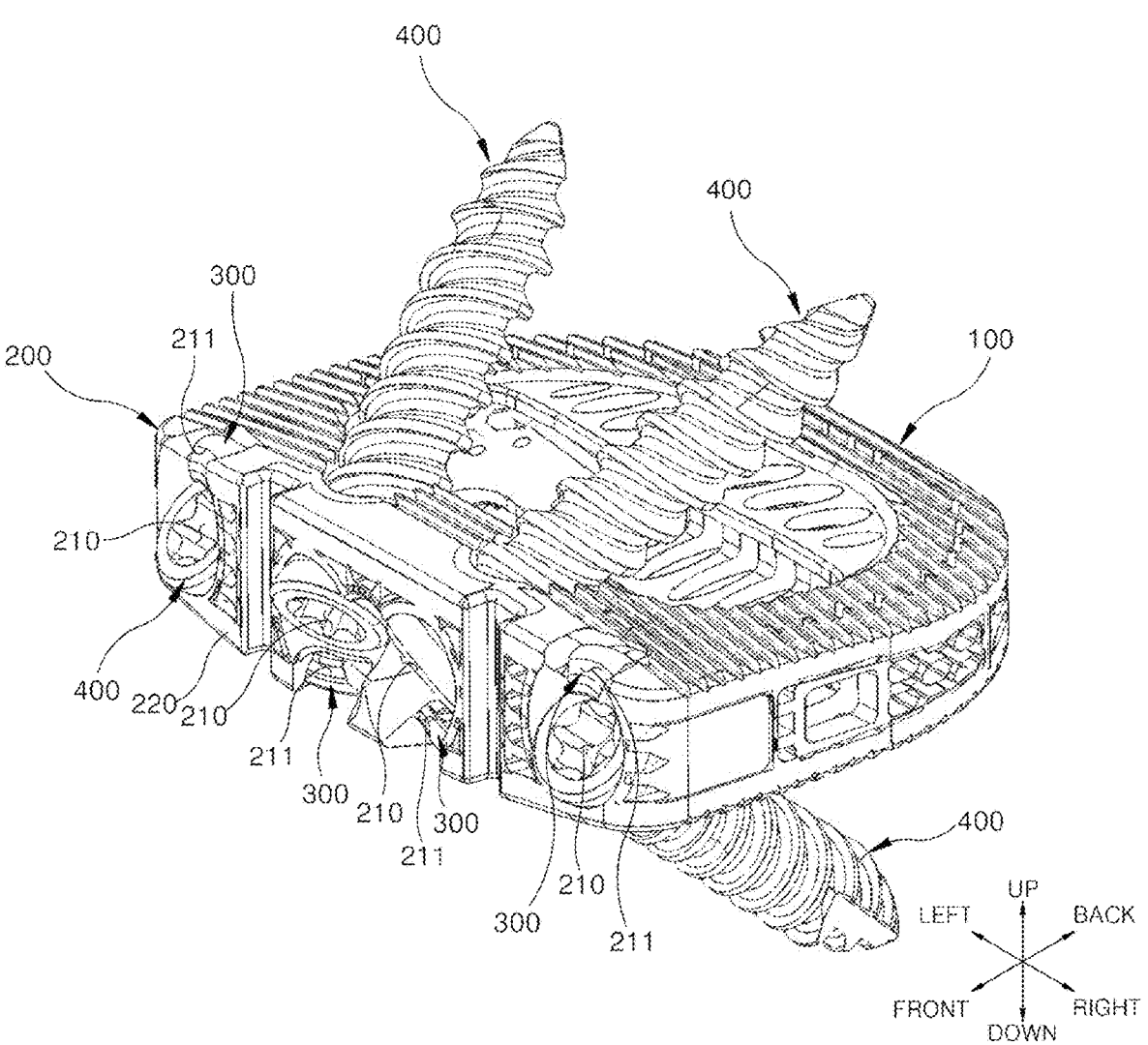
Figure 11:
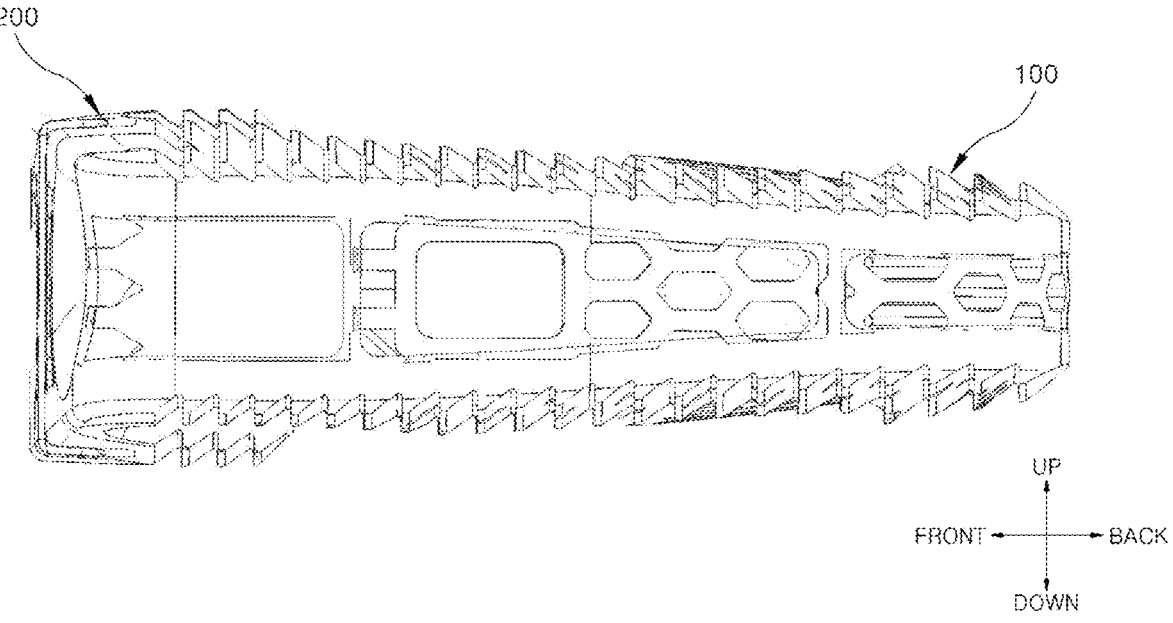
Figure 12:
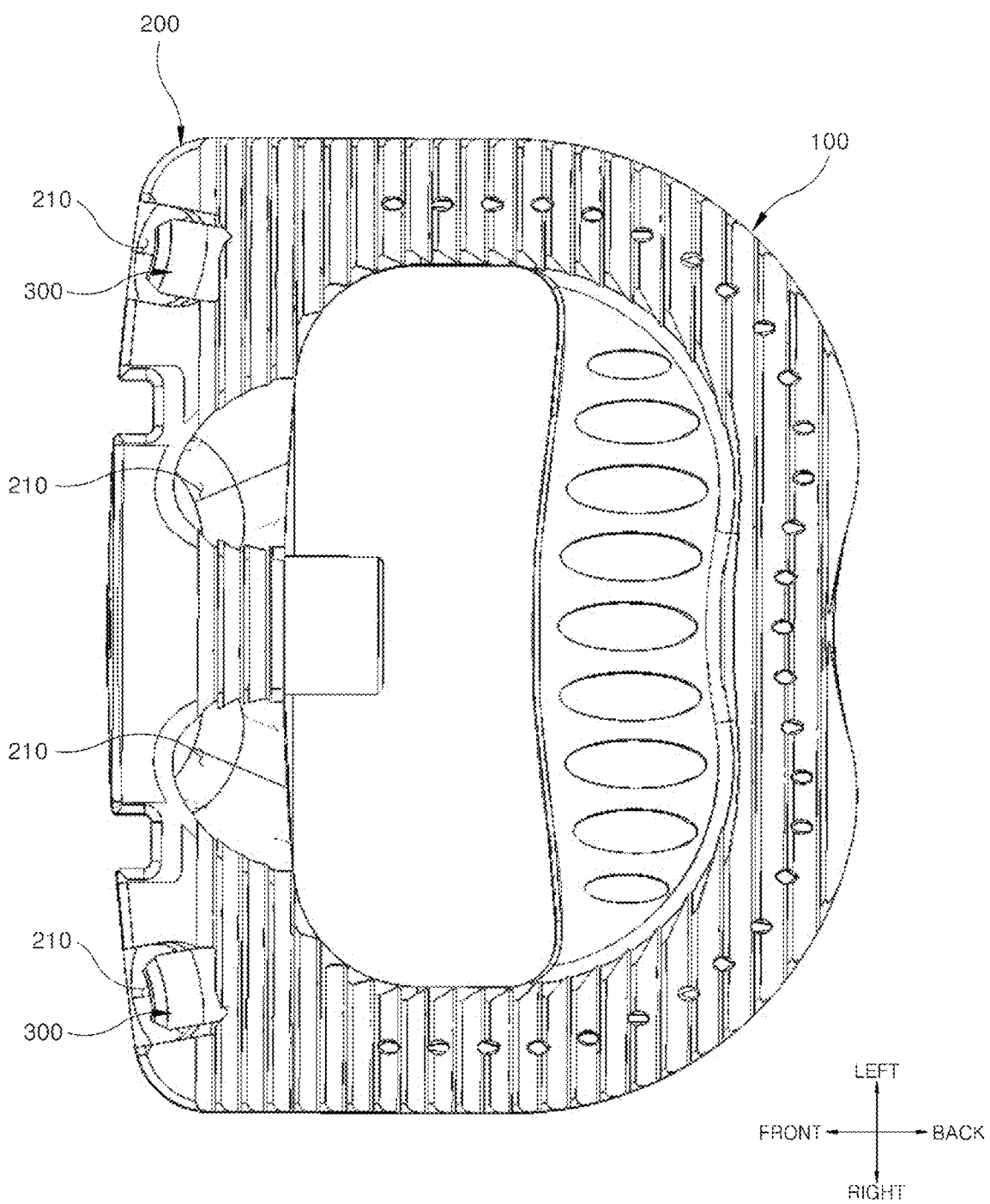
Figure 13:
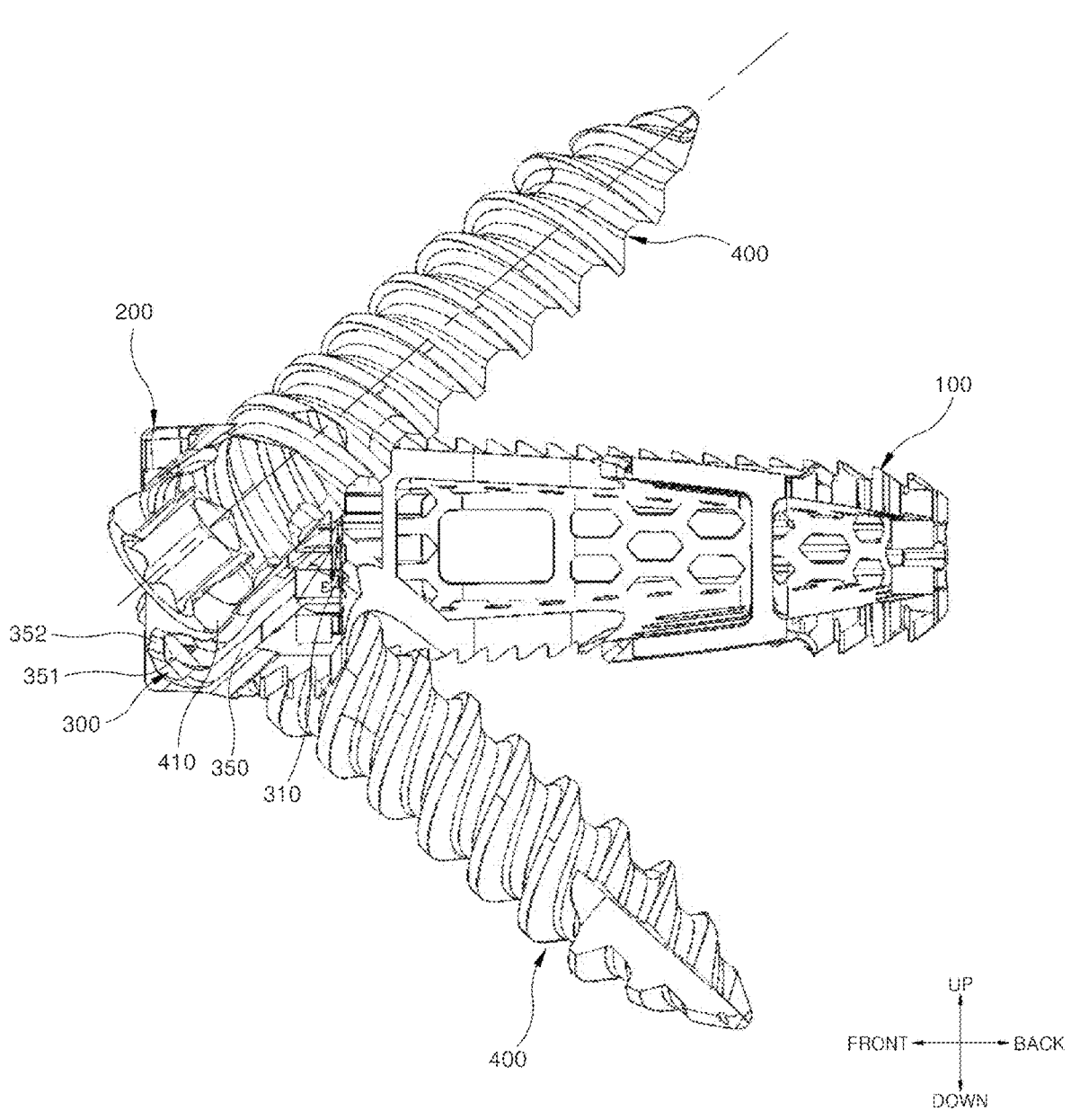
Figure 14:
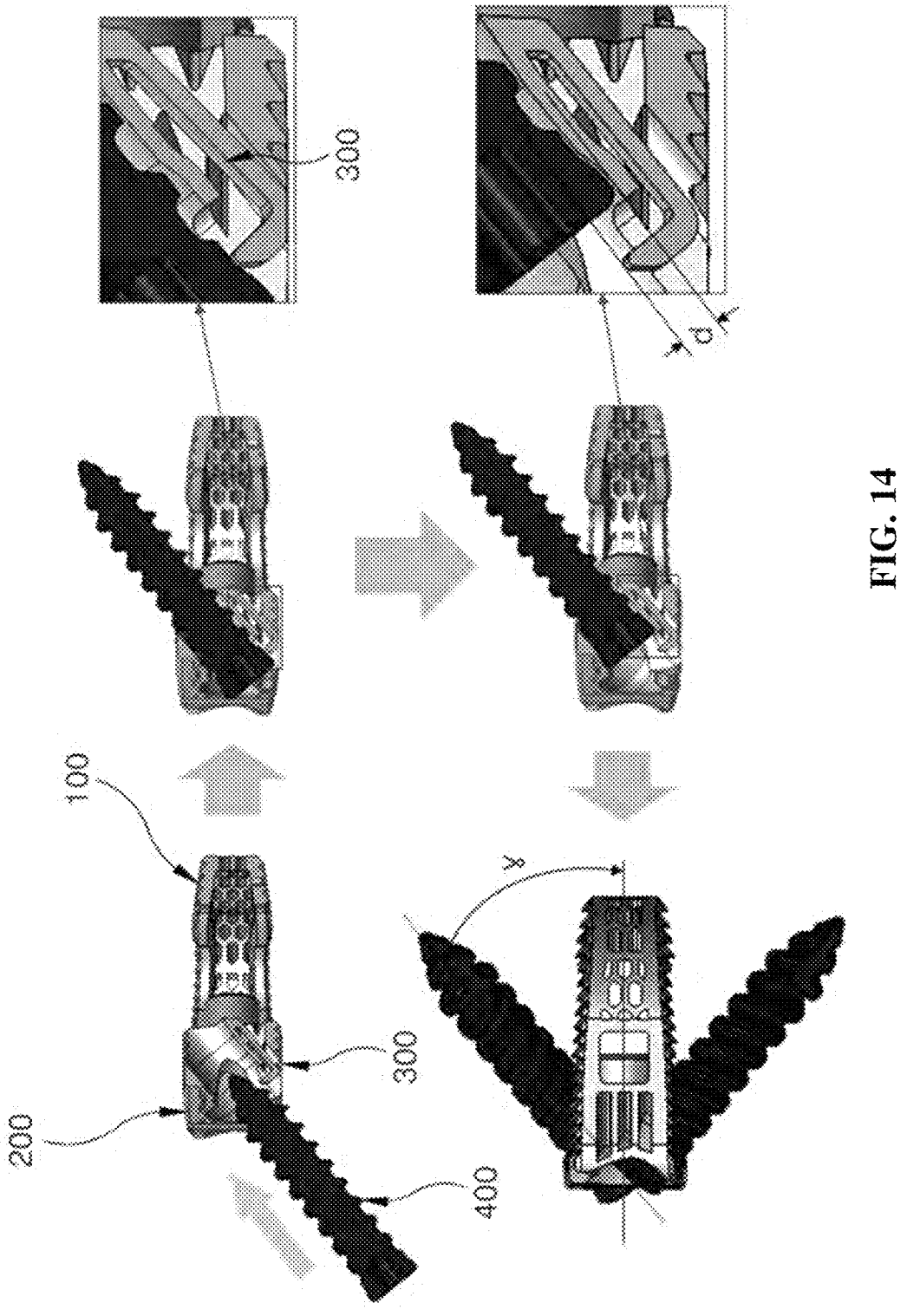
Figure 15:
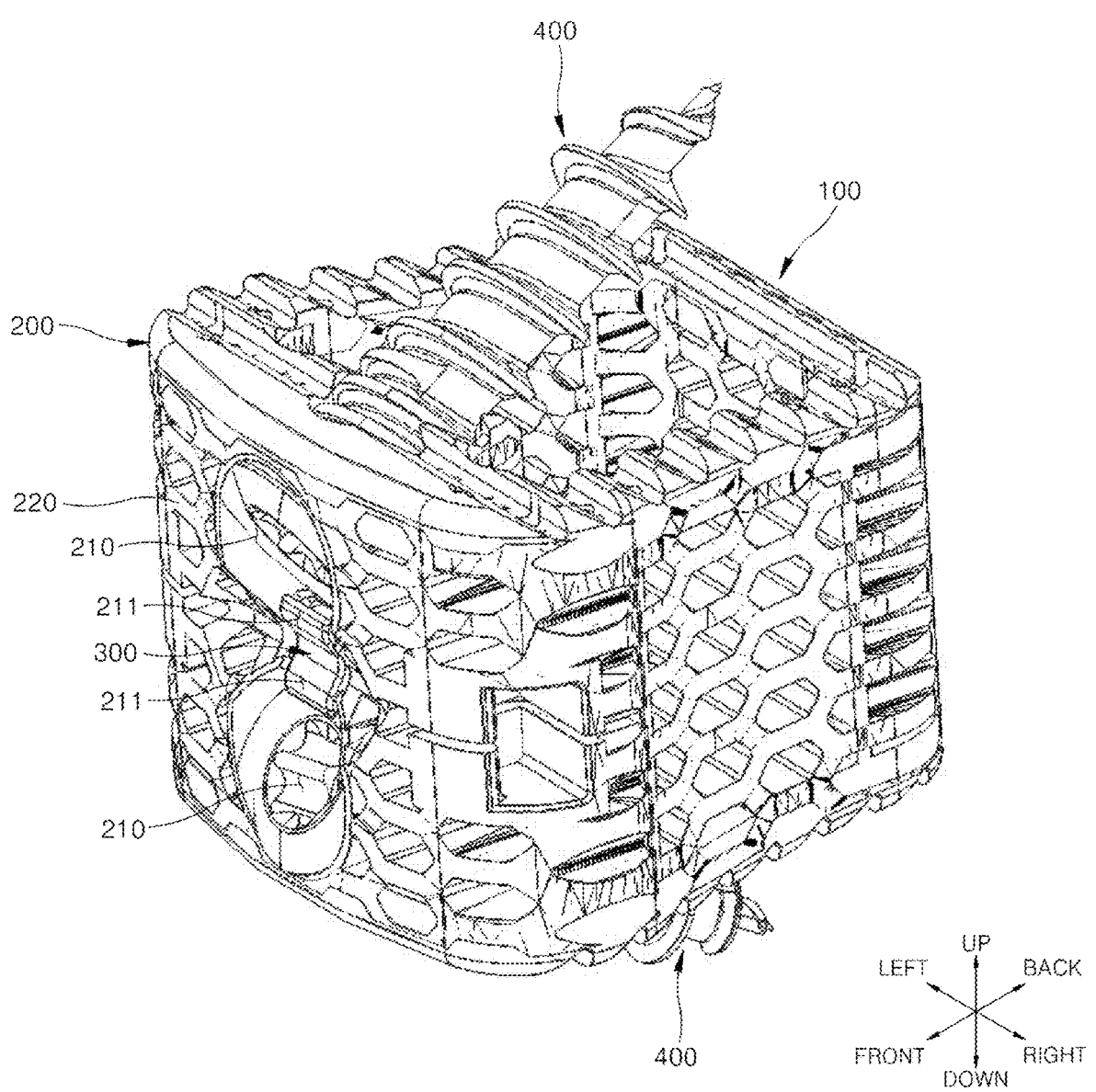
Figure 16:
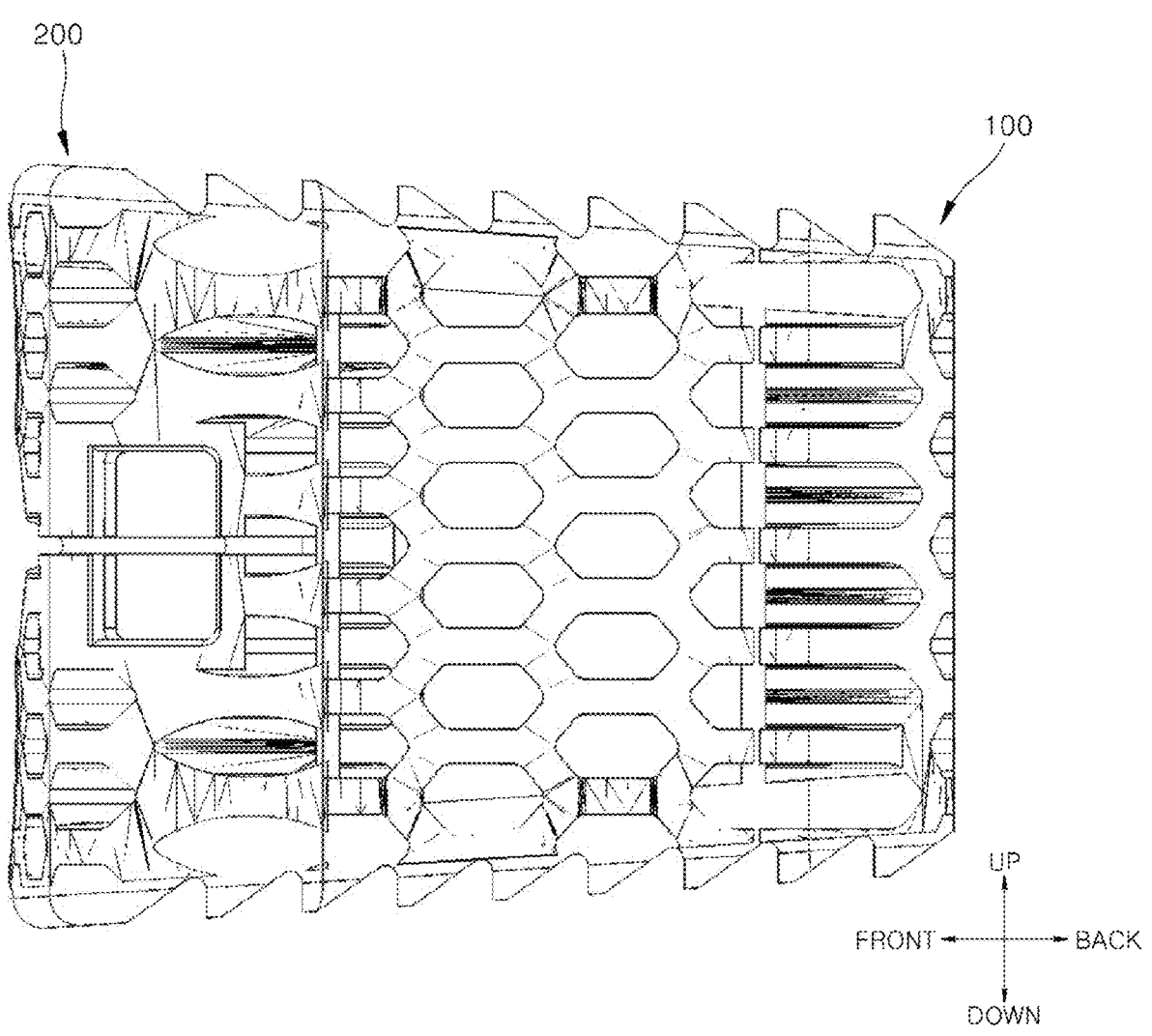
Figure 17:
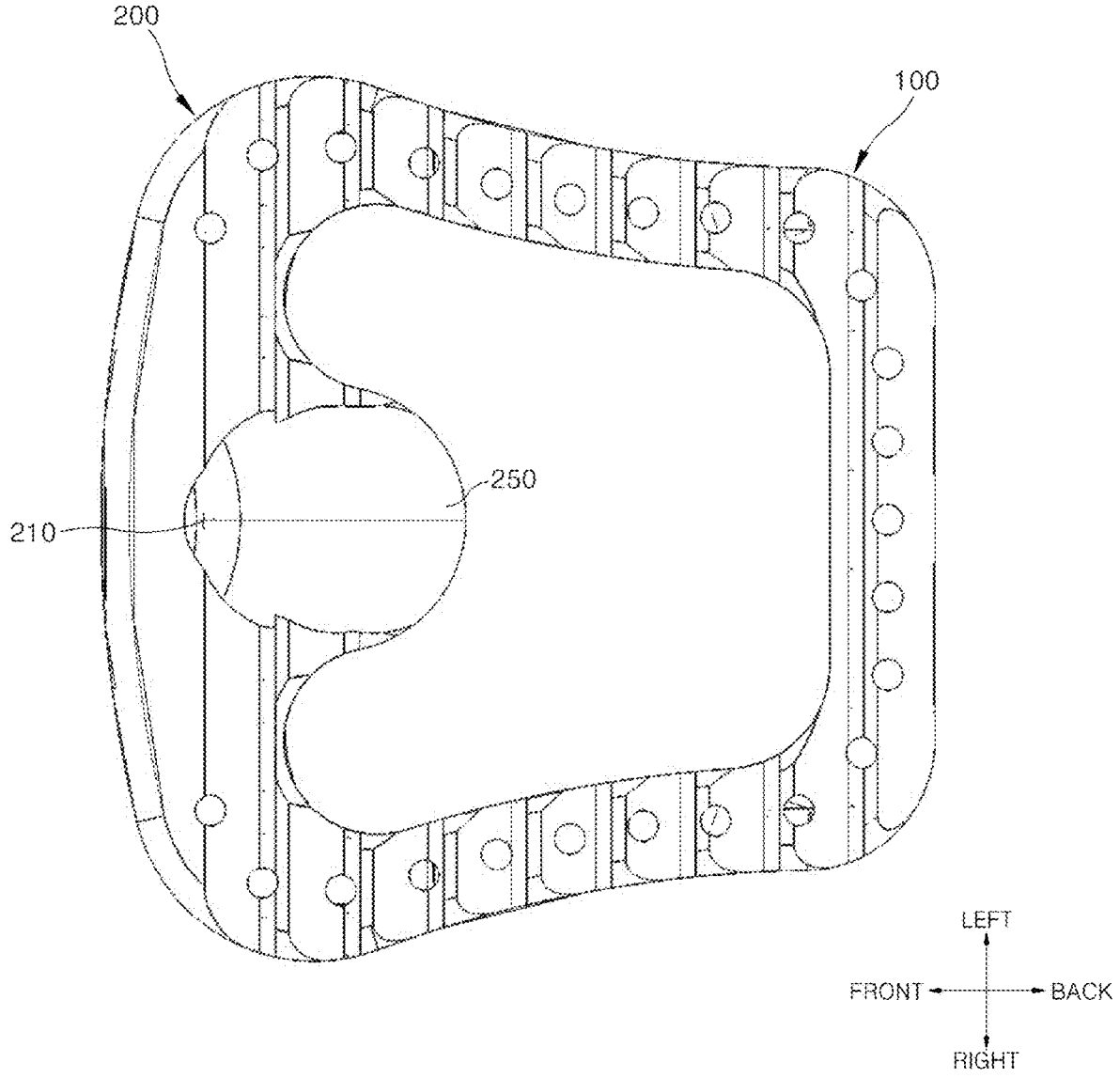
Figure 18:
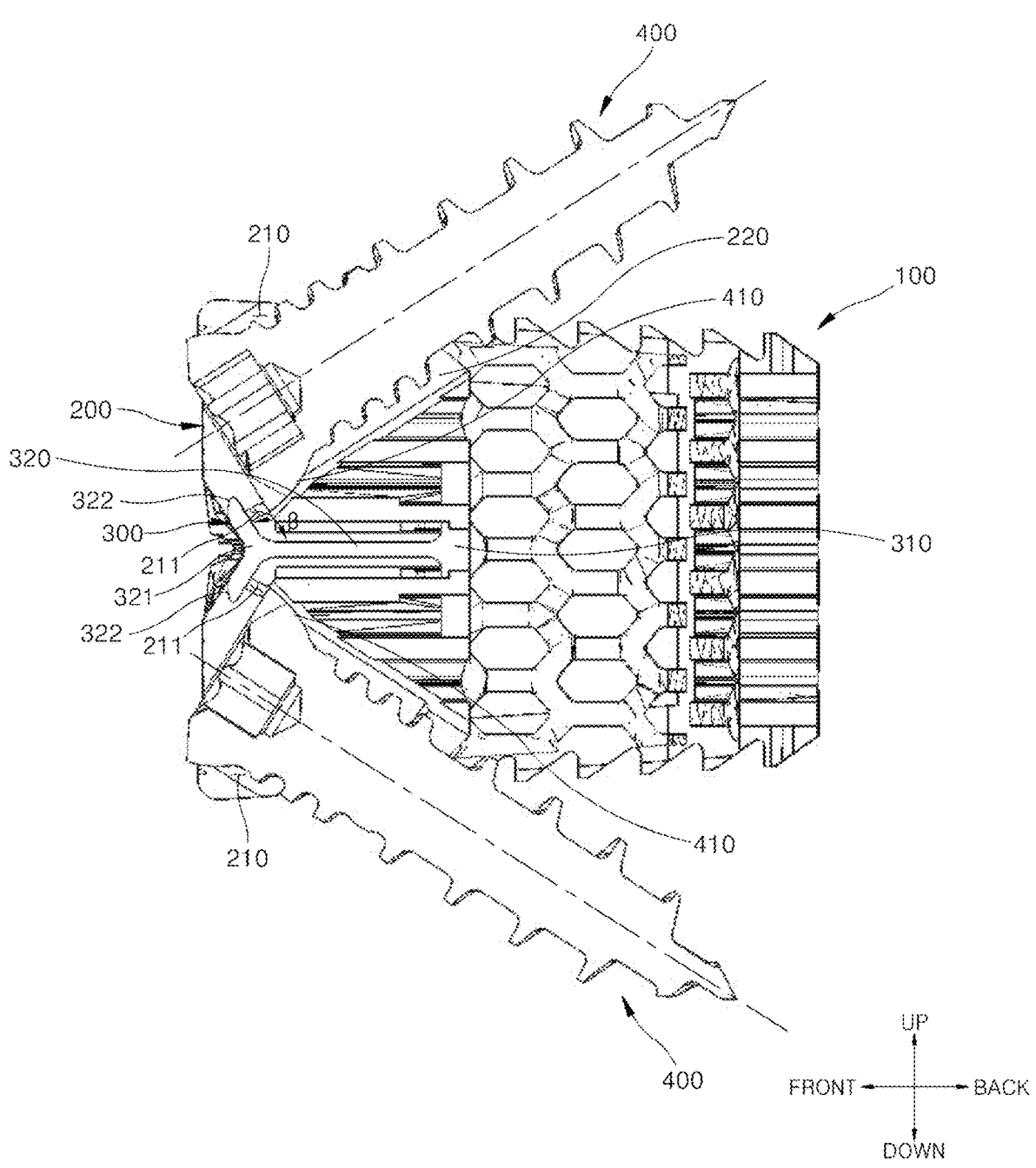

FIG. 3 is a plan view showing the spinal cage fixable through insertion of the bone screws according to the first embodiment of the present invention;

FIG. 4 is an anteroposterior cross-sectional view showing the spinal cage fixable through insertion of the bone screws according to the first embodiment of the present invention;

FIG. 5 is a view showing a combining process of the spinal cage fixable through insertion of the bone screws according to the first embodiment of the present invention;

FIG. 6 is a perspective view showing the overall appearance of a spinal cage fixable through insertion of bone screws according to a second embodiment of the present invention;

FIG. 7 is a side view showing the spinal cage fixable through insertion of the bone screws according to the second embodiment of the present invention;

FIG. 8 is a plan view showing the spinal cage fixable through insertion of the bone screws according to the second embodiment of the present invention;

FIG. 9 is an anteroposterior cross-sectional view showing the spinal cage fixable through insertion of the bone screws according to the second embodiment of the present invention;

FIG. 10 is a perspective view showing the overall appearance of a spinal cage fixable through insertion of bone screws according to a third embodiment of the present invention;

FIG. 11 is a side view showing the spinal cage fixable through insertion of the bone screws according to the third embodiment of the present invention;

FIG. 12 is a plan view showing the spinal cage fixable through insertion of the bone screws according to the third embodiment of the present invention;

FIG. 13 is an anteroposterior cross-sectional view showing the spinal cage fixable through insertion of the bone screws according to the third embodiment of the present invention;

FIG. 14 is a view showing a combining process of the spinal cage fixable through insertion of the bone screws according to the third embodiment of the present invention;

FIG. 15 is a perspective view showing the overall appearance of a spinal cage fixable through insertion of bone screws according to a fourth embodiment of the present invention;

FIG. 16 is a side view showing the spinal cage fixable through insertion of the bone screws according to the fourth embodiment of the present invention;

FIG. 17 is a plan view showing the spinal cage fixable through insertion of the bone screws according to the fourth embodiment of the present invention; and FIG. 18 is an anteroposterior cross-sectional view showing the spinal cage fixable through insertion of the bone screws according to the fourth embodiment of the present invention.

DETAILED DESCRIPTION OF THE INVENTION

Hereinafter, the present invention will be described detail based on the accompanying drawings to fully convey the scope of the present invention to those skilled in the art to which the present invention pertains. However, the present invention may be implemented in many different forms and is not limited to the embodiments described herein.

In order to clearly explain the present invention, parts that are not relevant to the description will be omitted, and the same or similar components will be indicated by the same reference numerals throughout the description.

In addition, terms or words used in the description and the claims should not be construed as limited to their usual or dictionary meanings, and should be interpreted as meanings and concepts consistent with the technical idea of the present invention based on the principle in which an inventor may appropriately define the concept of a term to explain his or her invention in the best way.

Figure 1:
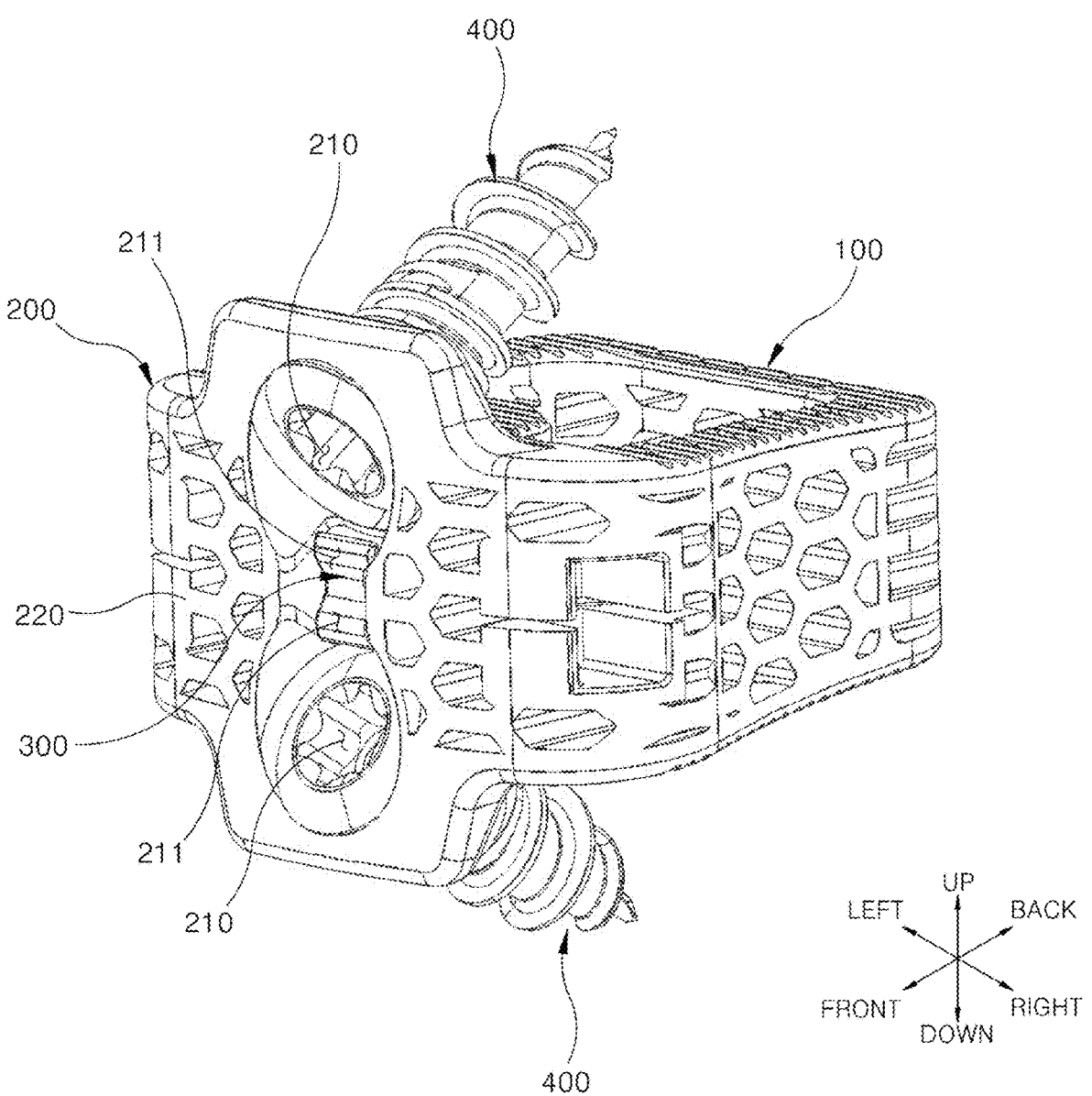
FIG. 1 is a perspective view showing the overall appearance of a spinal cage fixable through insertion of bone screws according to a first embodiment of the present invention.
Figure 2:
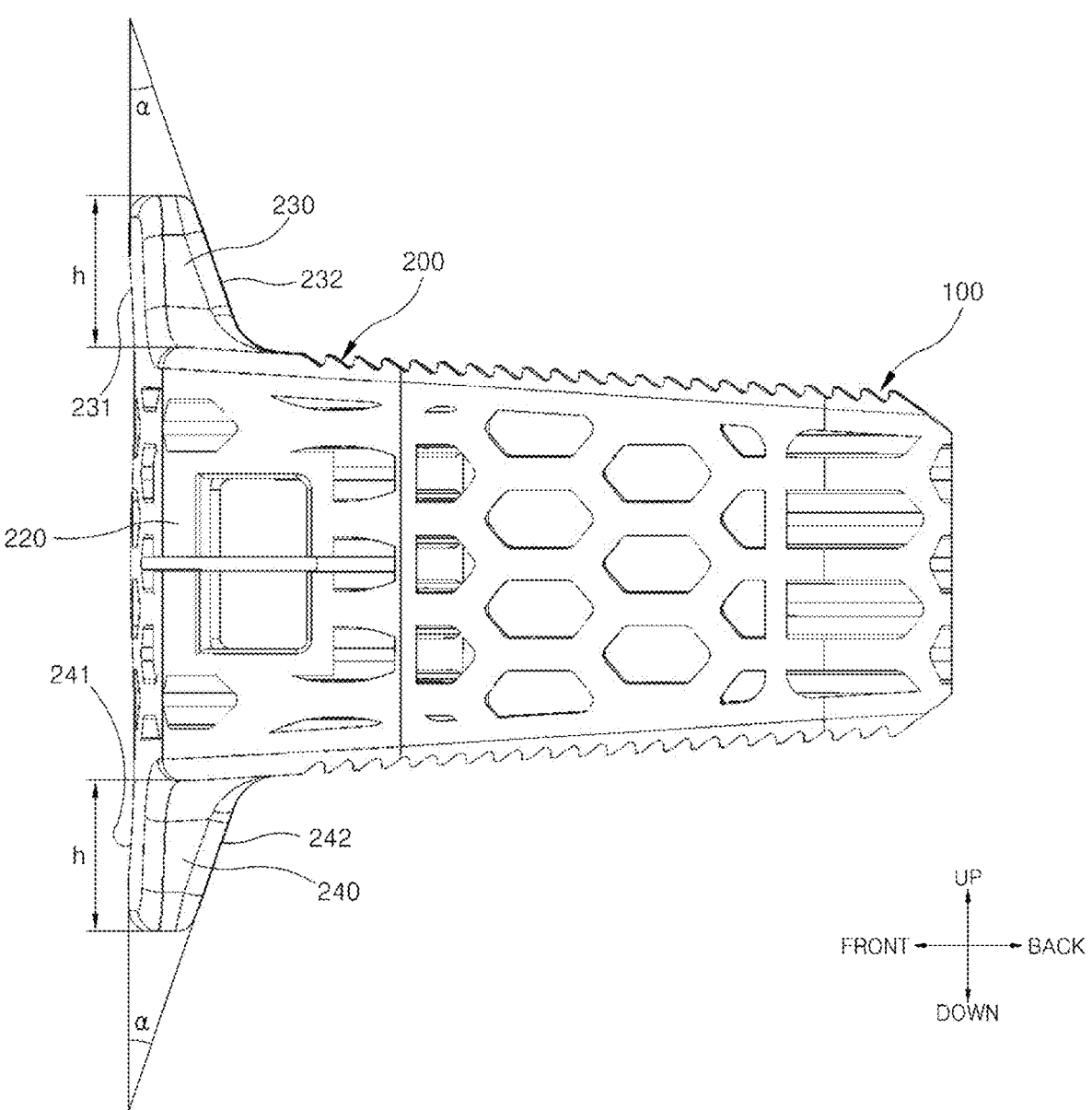
FIG. 2 is a side view showing the spinal cage fixable through insertion of the bone screws according to the first embodiment of the present invention.

FIG. 1 is a perspective view showing the overall appearance of a spinal cage fixable through insertion of bone screws according to a first embodiment of the present invention, FIG. 2 is a side view showing the spinal cage fixable through insertion of the bone screws according to the first embodiment of the present invention, FIG. 3 is a plan view showing the spinal cage fixable through insertion of the bone screws according to the first embodiment of the present invention, FIG. 4 is an anteroposterior cross-sectional view showing the spinal cage fixable through insertion of the bone screws according to the first embodiment of the present invention, and FIG. 5 is a view showing a combining process of the spinal cage fixable through insertion of the bone screws according to the first embodiment of the present invention.

As shown in these figures, the spinal cage fixable through insertion of the bone screws according to the first embodiment of the present invention includes a cage body 100, a receiver 200, and a fixture 300, and is inserted between vertebral bodies, such as cervical vertebrae and lumbar vertebrae, to maintain a distance between the vertebral bodies and to secure a space into which the bone grows and enters for fusion.

A hollow is formed in the central portion of the cage body 10, and the hollow is filled with an autograft, an allograft, or synthetic bone to promote bone growth.

The cage body 100 may include a polymer material as a main component of the cage body 100, and in addition, various additives or filling materials may be added thereto.

The receiver 200 is disposed on the front surface of the cage body 100, and is provided with a plurality screw holes 210 formed therein so that bone screws 400 are inserted into the screw holes 210. In the illustrated embodiment, two screw holes 210 are provided, but the number of the screw holes 210 is not limited thereto.

The bone screws 400 are inserted obliquely into the screw holes 210 to have a predetermined inclination angle with respect to the cage body 100 and the receiver 200, and among the bone screws 400 inserted into the screw holes 210, the bone screw 400 disposed in an upper area is inserted into a vertebral body located on the cage body 100, and the bone screw 400 disposed in a lower area is inserted into a vertebral body located under the cage body 100.

The fixture 300 is coupled to the receiver 200 adjacent to the screw holes 210, and may selectively block a portion of each screw hole 210. The front end of the fixture 300 is moved in the inward direction of the screw hole 210 when the bone screw 400 enters the hole screw 210, and the front end of the fixture 300 is moved in the outward direction of the screw hole 210 to prevent separation of the bone screw 400 from the screw hole 210 when insertion of the bone screw 400 has been completed.

The receiver 200 may be formed integrally with the cage body 100, or may be formed separately from the cage body 100 and coupled to the cage body 100. Since the receiver 200 surrounds the outer surfaces of the bone screws 400 to support the bone screws 400, the bone screws 400 may be fixed without any additional parts.

The receiver 200 includes a receiving body 220 disposed in front of the cage body 100, an upper protrusion 230 which protrudes upward from the upper surface of the receiving body 220 and is provided with the screw hole 210 formed therein, a lower protrusion 240 which protrudes downward from the lower surface of the receiving body 220 and is provided with the screw hole 210 formed therein, and a coupling protrusion 250 which protrudes backward from the rear surface of the receiving body 220 and is provided with a space formed therein so that the fixture 300 may be coupled thereto.

The upper protrusion 230 and the lower protrusion 240 have a sufficient size so that the bone screws 400 may be inserted into the screw holes 210 to be supported thereby. For example, the vertical height h of the upper protrusion 230 and the lower protrusion 240 may be 1 mm to 15 mm.

If the vertical height h of the upper protrusion 230 and the lower protrusion 240 is less than 1 mm, sufficient spaces to support the bone screws 400 may not be created, and if the vertical height h of the upper protrusion 230 and the lower protrusion 240 exceeds 15 mm, too much of surrounding vertebral bodies must be removed during spinal surgery.

A rear surface 232 of the upper protrusion 230 is formed as an inclined surface having a predetermined inclination angle α with respect to a front surface 231 so that the width of the upper protrusion 230 in the forward and rearward directions gradually decreases toward the upper end of the upper protrusion 230, and a rear surface 242 of the lower protrusion 240 is formed as an inclined surface having the predetermined inclination angle α with respect to a front surface 241 so that the width of the lower protrusion 240 in the forward and rearward directions gradually decreases toward the lower end of the lower protrusion 240.

That is, as shown in FIG. 2, the upper protrusion 230 and the lower protrusion 240 has a shape similar to a right triangle when viewed from the side, and surround the front portions of the bone screws 400.

The inclination angle α of the rear surfaces 232 and 242 of the upper protrusion 230 and the lower protrusion 240 may be 1° to 60°. The bone screws 400 are obliquely inserted into the cage body 100 and fastened to the vertebral body located in the upper area and the vertebral body located in the lower area, respectively, and the inclination angle α of the rear surfaces 232 and 242 of the upper protrusion 230 and the lower protrusion 240 is determined considering the insertion angle of the bone screws 400.

As shown in FIG. 4, the fixture 300 includes a support 310 which is longitudinally coupled to the inside of the coupling protrusion 250 of the receiver 200, an extension 320 which extends forward from the front surface of the support 310 and is orthogonal to the support 310, and an upper and lower restraint part 321 which extends from the front end of the extension 320 to have a predetermined upward inclination angle β and a predetermined downward inclination angle β. That is, the fixture 300 is formed as a hole in a "Y" shape.

The extension 320 is formed of an elastic material, and may thus be deformed up and down when external force is applied thereto. An internal space is formed inside the coupling protrusion 250 so that the extension 320 may be deformed up and down therein. The extension 320 may have a thickness of about 0.1 to 10 mm and a length of 0.1 to 20 mm to utilize elastic force.

In order to prevent separation of the bone screws 400 through deformation of the extension 320 up and down, the extension 320 must have a certain length to utilize elastic force, and accordingly, a space to secure a certain distance is required in the receiver 200.

The upward inclination angle β and the downward inclination angle β of the upper and lower restraint part 321 are determined so that the upper and lower restraint part 321 is disposed orthogonally to the central axes of the screw holes 210 and the bone screws 400 (indicted by an alternating long and short dashed line in the drawings). Here, the extension 320 is disposed horizontally.

Entry ends 211 are formed at the lower end of the screw hole 210 formed in the upper protrusion 230 and the upper end of the screw hole 210 formed in the lower protrusion 240 by cutting so that the upper and lower restraint part 321 may enter in the inward directions of the screw holes 210 therethrough.

When the extension 320 is disposed horizontally, a length d of an end of the upper and lower restraint part 321 inserted into the screw hole 210 may be 1 mm to 5 mm. If the length d of the end of the upper and lower restraint part 321 inserted into the screw hole 210 is less than 1 mm, a function of preventing separation of the bone screws 400 may not be sufficient performed, and if the length d of the end of the upper and lower restraint part 321 inserted into the screw hole 210 exceeds 5 mm, the path of the bone screw 400 is blocked when the bone screw 400 enters the screw hole 210 and it is difficult for the bone screw 400 to properly enter the screw hole 210.

Inclined ends 322 are formed at the front ends of the upper and lower restraint part 321. The inclined end 322 comes into contact with a screw protruding surface 410 formed on the side surface of the bone screw 400 when the bone screw 400 enters the screw hole 210, and as the screw protruding surface 410 of the bone screw 400 pushes the inclined end 322, the extension 320 is deformed up or down.

The opposite front ends of the upper and lower restraint part 321, where the inclined ends 322 are not disposed, are disposed parallel to the front ends of the bone screws 400, and thus, the bone screws 400, insertion of which into the screw holes 210 has been completed, are blocked by the upper and lower restraint part 21 not to be arbitrarily separated from the screw holes 210.

As shown in FIG. 5, when the bone screw 400 enters the screw hole 210, the extension 320 is deformed up or down and the upper and lower restraint part 321 is moved in the outward direction of the screw hole 210, and when insertion of the bone screw 400 into the screw hole 210 has been completed, the extension 320 returns to the original form thereof (i.e., is disposed horizontally) and the upper and lower restraint part 321 is moved in the inward direction of the screw hole 210.

After insertion of the bone screw 400 into the screw hole 210 has been completed, the bone screw 400 is obliquely coupled to the cage body 100, and an inclination angle γ of the bone screw 400 with respect to the cage body 100 is about 10° to 55°.

At this time, among the screw holes 210 formed in the receiver 200, the bone screw 400 entering the screw hole 210 disposed in the upper area and the bone screw 400 entering the screw hole 210 disposed in the lower area may not enter at the same time and may enter sequentially.

That is to say, when the bone screw 400 enters the screw hole 210 disposed in the upper area among the screw holes 210 formed in the receiver 200, the extension 320 is deformed downward, and the upper end of the upper and lower restraint part 321 is moved in the outward direction of the screw hole 210 disposed in the upper area, but the lower end of the upper and lower restraint part 321 is moved in the inward direction of the screw hole 210 disposed in the lower area and blocks the screw hole 210 disposed in the lower area, and therefore, it is impossible for the bone screw 400 to enter the screw hole 210 disposed in the lower area.

In the same manner, when the bone screw 400 enters the screw hole 210 disposed in the lower area among the screw holes 210 formed in the receiver 200, the extension 320 is deformed upward, and the lower end of the upper and lower restraint part 321 is moved in the outward direction of the screw hole 210 disposed in the lower area, but the upper end of the upper and lower restraint part 321 is moved in the inward direction of the screw hole 210 disposed in the upper area and blocks the screw hole 210 disposed in the upper area, and therefore, it is impossible for the bone screw 400 to enter the screw hole 210 disposed in the upper area.

As shown in FIG. 4, when insertion of the bone screws 400 into the screw hole 210 disposed in the upper area and the screw hole 210 disposed in the lower area out of the screw holes 210 formed in the receiver 200 has been completed, the upper and lower restraint part 321 blocks the screw holes 210 so that a pair of bone screws 400 inserted into the upper and lower portions of the receiver 200 is not separated from the screw holes 210.

FIG. 6 is a perspective view showing the overall appearance of a spinal cage fixable through insertion of bone screws according to a second embodiment of the present invention, FIG. 7 is a side view showing the spinal cage fixable through insertion of the bone screws according to the second embodiment of the present invention, FIG. 8 is a plan view showing the spinal cage fixable through insertion of the bone screws according to the second embodiment of the present invention, and FIG. 9 is an anteroposterior cross-sectional view showing the spinal cage fixable through insertion of the bone screws according to the second embodiment of the present invention.

In the same manner as the spinal cage fixable through insertion of the bone screws according to the first embodiment of the present invention, the spinal cage fixable through insertion of the bone screws according to the second embodiment of the present invention includes a cage body 100, a receiver 200, and a fixture 300.

The spinal cage fixable through insertion of the bone screws according to the second embodiment of the present invention is suitable for the cage body 100 having a greater height than that of the spinal cage fixable through insertion of the bone screws according to the first embodiment of the present invention.

The receiver 200 is disposed on the front surface of the cage body 100, and is provided with a plurality of screw holes 210 formed therein so that bone screws 400 pass through the screw holes 210 to be inserted thereinto. The bone screws 400 are inserted obliquely into the screw holes 210 to have a predetermined inclination angle with respect to the cage body 100 and the receiver 200.

The fixture 300 is coupled to the receiver 200 adjacent to the screw holes 210, and may selectively block a portion of each screw hole 210. The receiver 200 may be formed integrally with the cage body 100, or may be formed separately from the cage body 100 and coupled to the cage body 100. Since the receiver 200 surrounds the outer surfaces of the bone screws 400 to support the bone screws 400, the bone screws 400 may be fixed without any additional parts.

The receiver 200 includes a receiving body 220 disposed in front of the cage body 100, an upper protrusion 230 which protrudes upward from the upper surface of the receiving body 220 and is provided with the screw hole 210 formed therein, a lower protrusion 240 which protrudes downward from the lower surface of the receiving body 220 and is provided with the screw hole 210 formed therein, and a coupling protrusion 250 which protrudes backward from the rear surface of the receiving body 220 and is provided with a space formed therein so that the fixture 300 may be coupled thereto.

In the same manner as the upper protrusion 230 according to the first embodiment of the present invention, a rear surface 232 of the upper protrusion 230 is formed as an inclined surface having a predetermined inclination angle α with respect to a front surface 231 so that the width of the upper protrusion 230 in the forward and rearward directions gradually decreases toward the upper end of the upper protrusion 230, and a rear surface 242 of the lower protrusion 240 is formed as an inclined surface having the predetermined inclination angle α with respect to a front surface 241 so that the width of the lower protrusion 240 in the forward and rearward directions gradually decreases toward the lower end of the lower protrusion 240.

As shown in FIG. 9, the fixture 300 includes a support 310 which is longitudinally coupled to the inside of the coupling protrusion 250 of the receiver 200, a first extension 330 which extends forward from the upper portion of the front surface of the support 310 and is orthogonal to the support 310, a second extension 340 which extends forward from the lower portion of the front surface of the support 310 and is orthogonal to the support 310, an upper restraint part 331 which extends from the front end of the first extension 330 to have a predetermined upward inclination angle 81, and a lower restraint part 341 which extends from the front end of the second extension 340 to have a predetermined downward inclination angle 82.

That is to say, in contrast to the extension 320 according to the first embodiment of the present invention, the first extension 330 and the second extension 340 according to the second embodiment of the present invention are separated up and down, and the upper restraint part 331 and the first extension 330 extending therefrom and the lower restraint part 341 and the second extension 340 extending therefrom are formed as a whole in the shape of a straight line with a curved end.

The first extension 330 and the second extension 340 are formed of an elastic material, and may thus be deformed up and down when external force is applied thereto. An internal space is formed inside the coupling protrusion 250 so that the first extension 330 and the second extension 340 may be deformed up and down therein. The upward inclination angle 81 of the upper restraint part 331 and the lower inclination angle 82 of the lower restraint part 341 are determined so that the upper restraint part 331 and the lower restraint part 341 are disposed orthogonally to the central axes of the screw holes 210 and the bone screws 400 (indicted by an alternating long and short dashed line in the drawings). Here, the first extension 330 and the second extension 340 are disposed horizontally.

The upward inclination angle 81 of the upper restraint part 331 and the lower inclination angle 82 of the lower restraint part 341 may be the same or may be different depending on the situation. When the upward inclination angle 81 of the upper restraint part 331 and the lower inclination angle 82 of the lower restraint part 341 are different, the bone screws 400 inserted into the screw holes 210 may also be disposed at different angles.

Entry ends 211 are formed at the lower end of the screw hole 210 formed in the upper protrusion 230 and the upper end of the screw hole 210 formed in the lower protrusion 240 by cutting so that the upper restraint part 331 and the lower restraint part 341 may enter in the inward directions of the screw holes 210 therethrough.

Inclined ends 332 and 342 are formed at front ends of the upper restraint part 331 and the lower restraint part 341. The inclined ends 332 and 342 come into contact with screw protruding surfaces 410 formed on the side surfaces of the bone screws 400 when the bone screws 400 enter the screw holes 210, and as the screw protruding surfaces 410 of the bone screws 400 push the inclined ends 332 and 342, the first extension 330 and the second extension 340 are deformed up and down.

When the bone screws 400 enter the screw holes 210, the first extension 330 is deformed downward and the upper restraint portion 331 is moved in the outward direction of one corresponding screw hole 210, the second extension 340 is deformed upward and the lower restraint portion 341 is moved in the outward direction of the other corresponding screw hole 210, and when insertion of the bone screws 400 into the screw holes 210 has been completed, the first extension 330 and the second extension 340 return to the original form thereof (i.e., are disposed horizontally) and the upper restraint part 331 and the lower restraint part 341 are moved in the inward directions of the respective screw holes 210.

Unlike the spinal cage fixable through insertion of the bone screws according to the first embodiment of the present invention, in the spinal cage fixable through insertion of the bone screws according to the second embodiment of the present invention, among the screw holes 210 formed in the receiver 200, the bone screw 400 entering the screw hole 210 disposed in the upper area and the bone screw 400 entering the screw hole 210 disposed in the lower area may not enter at the same time.

The cage body 100 according to the second embodiment of the present invention has a greater height than the cage body 100 according to the first embodiment of the present invention and thus provides a sufficient space to which the first extension 330 and the second extension 340 are coupled, and the first extension 330 and the second extension 340 may be deformed independently and thus a pair of bone screws 400 may enter the screw holes 210 at the same time.

As shown in FIG. 9, when insertion of the bone screws 400 into the screw hole 210 disposed in the upper area and the screw hole 210 disposed in the lower area out of the screw holes 210 formed in the receiver 200 has been completed, the upper restraint part 331 blocks the screw hole 210 disposed in the upper area so that the bone screw 400 inserted into the corresponding screw hole 210 is not separated from the screw hole 210, and the lower restraint part 341 blocks the screw hole 210 disposed in the lower area so that the bone screw 400 inserted into the corresponding screw hole 210 is not separated from the screw hole 210.

FIG. 10 is a perspective view showing the overall appearance of a spinal cage fixable through insertion of bone screws according to a third embodiment of the present invention, FIG. 11 is a side view showing the spinal cage fixable through insertion of the bone screws according to the third embodiment of the present invention, FIG. 12 is a plan view showing the spinal cage fixable through insertion of the bone screws according to the third embodiment of the present invention, FIG. 13 is an anteroposterior cross-sectional view showing the spinal cage fixable through insertion of the bone screws according to the third embodiment of the present invention, and FIG. 14 is a view showing a combining process of the spinal cage fixable through insertion of the bone screws according to the third embodiment of the present invention.

In the same manner as the spinal cage fixable through insertion of the bone screws according to the first embodiment of the present invention and the spinal cage fixable through insertion of the bone screws according to the second embodiment of the present invention, the spinal cage fixable through insertion of the bone screws according to the third embodiment of the present invention includes a cage body 100, a receiver 200, and a fixture 300.

The receiver 200 is disposed on the front surface of the cage body 100, and is provided with a plurality of screw holes 210 formed therein so that bone screws 400 pass through the screw holes 210 to be inserted thereinto. The bone screws 400 are inserted obliquely into the screw holes 210 to have a predetermined inclination angle with respect to the cage body 100 and the receiver 200.

The spinal cage fixable through insertion of the bone screws according to the third embodiment of the present invention differs from the spinal cage fixable through insertion of the bone screws according to the first embodiment of the present invention in that the spinal cage fixable through insertion of the bone screws according to the third embodiment of the present invention includes a total of four bone screws 400 including two bone screws 400 inserted obliquely to the top and two bone screws 400 inserted obliquely to the bottom.

The fixture 300 is coupled to the receiver 200 adjacent to the screw holes 210, and may selectively block a portion of each screw hole 210. The receiver 200 may be formed integrally with the cage body 100, or may be formed separately from the cage body 100 and coupled to the cage body 100. Since the receiver 200 surrounds the outer surfaces of the bone screws 400 to support the bone screws 400, the bone screws 400 may be fixed without any additional parts.

The receiver 200 according to the third embodiment of the present invention differs from the receiver 200 according to the first embodiment of the present invention in that the upper protrusion 230 and the lower protrusion 240 are not formed.

As shown in FIG. 13, the fixture includes a support 310 which is longitudinally coupled to the inside of the receiver 200, an extended inclined part 350 which extends forward from the front portion of the support 310 to have a predetermined inclination angle & with respect to the support 310, and an orthogonal restraint part 351 which extends orthogonally to the front end of the extended inclined part 350.

While the extension 320 according to the first embodiment of the present invention and the first extension 330 and the second extension 340 according to the second embodiment of the present invention extend orthogonally to the support 310, the extended inclined part 350 according to the third embodiment of the present invention has the predetermined inclination angle & with respect to the support 310.

The extended inclined part 350 is formed of an elastic material, and may thus be deformed up and down when external force is applied thereto. An internal space is formed inside the receiver 200 so that the extended inclined part 350 may be deformed up and down therein.

The extended inclined part 350 is disposed parallel to the side surfaces of the screw holes 210. That is, the extended inclined part 350 is disposed parallel to the central axes of the screw holes 210 and the bone screws 400 (indicted by an alternating long and short dashed line in the drawings).

Since the orthogonal restraint part 351 extend orthogonally to the extended inclined part 350, the orthogonal restraint part 351 is disposed orthogonally to the central axes of the screw holes 210 and the bone screws 400.

Entry ends 211 are formed at the lower ends of the screw holes 210 or the upper ends of the screw holes 210 by cutting so that the orthogonal restraint part 351 may enter in the inward directions of the screw holes 210 therethrough.

An inclined end 352 is formed at the front end of the orthogonal restraint part 351. The inclined end 352 comes into contact with a screw protruding surface 410 formed on the side surface of the bone screw 400 when the bone screw 400 enters the screw hole 210, and as the screw protruding surface 410 of the bone screw 400 pushes the inclined end 352, the extended inclined part 350 is deformed up and down.

As shown in FIG. 14, when the bone screw 400 enters the screw hole 210, the extended inclined part 350 is deformed up or down and the orthogonal restraint part 351 is moved in the outward direction of the screw hole 210, and when insertion of the bone screw 400 into the screw hole 210 has been completed, the extended inclined part 350 is disposed parallel to the side surface of the screw hole 210 and the orthogonal restraint part 351 is moved in the inward direction of the screw hole 210.

When insertion of the bone screws 400 into all the screw holes 210 formed in the receiver 200 has been completed, the orthogonal restraint part 351 disposed adjacent to the respective screw holes 210 blocks the screw holes 210 so that the bone screws 400 inserted into the screw holes 210 are not separated from the screw holes 210.

FIG. 15 is a perspective view showing the overall appearance of a spinal cage fixable through insertion of bone screws according to a fourth embodiment of the present invention, FIG. 16 is a side view showing the spinal cage fixable through insertion of the bone screws according to the fourth embodiment of the present invention, FIG. 17 is a plan view showing the spinal cage fixable through insertion of the bone screws according to the fourth embodiment of the present invention, and FIG. 18 is an anteroposterior cross-sectional view showing the spinal cage fixable through insertion of the bone screws according to the fourth embodiment of the present invention.

The spinal cage fixable through insertion of the bone screws according to the fourth embodiment of the present invention includes a cage body 100, a receiver 200, and a fixture 300.

The spinal cage fixable through insertion of the bone screws according to the fourth embodiment of the present invention is suitable for the cage body 100 having a greater height than that of the spinal cage fixable through insertion of the bone screws according to the first embodiment of the present invention.

The receiver 200 is disposed on the front surface of the cage body 100, and is provided with a plurality of screw holes 210 formed therein so that bone screws 400 pass through the screw holes 210 to be inserted thereinto. The bone screws 400 are inserted obliquely into the screw holes 210 to have a predetermined inclination angle with respect to the cage body 100 and the receiver 200.

The fixture 300 is coupled to the receiver 200 adjacent to the screw holes 210, and may selectively block a portion of each screw hole 210. The receiver 200 may be formed integrally with the cage body 100, or may be formed separately from the cage body 100 and coupled to the cage body 100. Since the receiver 200 surrounds the outer surfaces of the bone screws 400 to support the bone screws 400, the bone screws 400 may be fixed without any additional parts.

The receiver 200 according to the fourth embodiment of the present invention differs from the receiver 200 according to the first embodiment of the present invention and the receiver 200 according to the second embodiment of the present invention in that the upper protrusion 230 and the lower protrusion 240 are not formed.

Specifically, the receiver 200 includes a receiving body 220 disposed in front of the cage body 100, and a coupling protrusion 250 which protrudes backward from the rear surface of the receiving body 220 and has a space formed therein so that the fixture 300 may be coupled thereto.

As shown in FIG. 18, the fixture 300 includes a support 310 which is longitudinally coupled to the inside of the coupling protrusion 250 of the receiver 200, an extension 250 which extends forward from the front surface of the support 310 and is orthogonal to the support 310, and an upper and lower restraint part 321 which extends from the front end of the extension 320 to have a predetermined upward inclination angle β and a predetermined downward inclination angle β. That is, the fixture 300 is formed as a hole in a "Y" shape.

The extension 320 is formed of an elastic material, and may thus be deformed up and down when external force is applied thereto. An internal space is formed inside the coupling protrusion 250 so that the extension 320 may be deformed up and down therein.

In order to prevent separation of the bone screws 400 through deformation of the extension 320 up and down, the extension 320 must have a certain length to utilize elastic force, and accordingly, a space to secure a certain distance is required in the receiver 200.

The upward inclination angle β and the downward inclination angle β of the upper and lower restraint part 321 are determined so that the upper and lower restraint part 321 is disposed orthogonally to the central axes of the screw holes 210 and the bone screws 400 (indicted by an alternating long and short dashed line in the drawings). Here, the extension 320 is disposed horizontally.

Entry ends 211 are formed at the lower end of the screw hole 210 formed in the upper protrusion 230 and the upper end of the screw hole 210 formed in the lower protrusion 240 by cutting so that the upper and lower restraint part 321 may enter in the inward directions of the screw holes 210 therethrough.

Inclined ends 322 are formed at the front ends of the upper and lower restraint part 321. The inclined end 322 comes into contact with a screw protruding surface 410 formed on the side surface of the bone screw 400 when the bone screw 400 enters the screw hole 210, and as the screw protruding surface 410 of the bone screw 400 pushes the inclined end 322, the extension 320 is deformed up or down.

The opposite front ends of the upper and lower restraint part 321, where the inclined ends 322 are not disposed, are disposed parallel to the front ends of the bone screws 400, and thus, the bone screws 400, insertion of which into the screw holes 210 has been completed, are blocked by the upper and lower restraint part 21 not to be arbitrarily separated from the screw holes 210.

When the bone screw 400 enters the screw hole 210, the extension 320 is deformed up or down and the upper and lower restraint part 321 is moved in the outward direction of the screw hole 210, and when insertion of the bone screw 400 into the receiver 200 through the screw hole 210 has been completed, the extension 320 returns to the original form thereof (i.e., is disposed horizontally) and the upper and lower restraint part 321 is moved in the inward direction of the screw hole 210.

As is apparent from the above description, a spinal cage fixable through insertion of bone screws according to the present invention may be fixed by inserting the bone screws into screw holes of a receiver without any separate parts, thereby making assembly simple and significantly reducing a time required for a procedure for fixing the spinal cage between vertebral bodies.

In addition, the spinal cage according to the present invention prevents the bone screws from being separated from the screw holes using a fixture installed adjacent to the screw holes, thereby eliminating the need for complicate processed products or assembled items when performing spinal surgery.

Although the embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A spinal cage configured to be fixed by bone screws, the spinal cage comprising:

a cage body;

a receiver disposed on a front surface of the cage body and including a plurality of screw holes for receiving the bone screws; and a fixture coupled to the receiver, adjacent to the plurality of screw holes, and configured to selectively block a portion of each of the plurality of screw holes, wherein, when each of the bone screws enters each of the plurality of screw holes, a front end of the fixture is moved in an outward direction of each of the plurality of screw holes, and when each bone screw is disposed in each of the plurality of screw holes, the front end of the fixture is moved in an inward direction of each of the plurality of screw holes to prevent each bone screw from being separated from each of the plurality of screw holes, wherein the fixture comprises:

a support longitudinally coupled to an inside of the receiver;

an extension including a first extension and a second extension, the first extension extending forward from an upper portion of a front surface of the support and disposed to be orthogonal to the support, and the second extension extending forward from a lower portion of the front surface of the support and disposed to be orthogonal to the support; and an upper and lower restraint part including an upper restraint part and a lower restraint part, the upper restraint part extending from a front end of the first extension to have an upward inclination angle, and the lower restraint part extending from a front end of the second extension to have a downward inclination angle.

2. The spinal cage according to claim 1, wherein the receiver comprises:

a receiving body disposed in front of the cage body;

an upper protrusion protruding upward from an upper surface of the receiving body and having one or more of the plurality of screw holes; and a lower protrusion protruding downward from a lower surface of the receiving body and having another one or more of the plurality of screw holes.

3. The spinal cage according to claim 2, wherein:

a rear surface of the upper protrusion includes an inclined surface having a a first inclination angle with respect to a front surface of the upper protrusion such that a width of the upper protrusion in forward and rearward directions gradually decreases toward an upper end of the upper protrusion; and a rear surface of the lower protrusion includes an inclined surface having a second inclination angle with respect to a front surface of the lower protrusion such that a width of the lower protrusion in the forward and rearward directions gradually decreases toward a lower end of the lower protrusion.

4. The spinal cage according to claim 2, wherein a vertical height of each of the upper protrusion and the lower protrusion is 1 mm to 15 mm.

5. The spinal cage according to claim 3, wherein each of the first and second inclination angles is 1° to 60°.

6. The spinal cage according to claim 1, wherein:

when each bone screw enters each of the plurality of screw holes, the corresponding extension is deformed up or down and the corresponding upper or lower restraint part is moved in the outward direction of each of the plurality of screw holes; and when each bone screw is disposed in each of the plurality of screw holes, the corresponding extension returns to an original form thereof and the corresponding upper or lower restraint part is moved in the inward direction of each of the plurality of screw holes.

7. The spinal cage according to claim 1, wherein the receiver includes an upper area and a lower area, and wherein, among the bone screws configured to be disposed in the plurality of screw holes in the receiver, a first bone screw configured to enter a first screw hole of the plurality of first screw holes, the first screw hole disposed in the upper area, and a second bone screw configured to enter a second screw hole of the plurality of screw holes, the second screw whole disposed in the lower area, are not configured to enter at the same time and are configured to enter sequentially.

8. The spinal cage according to claim 1, wherein the receiver includes an upper area and a lower area, the bone screws include a first bone screw and a second bone screw and the plurality of screw holes includes a first screw hole disposed in the upper area of the receiver and a second screw hole disposed in the lower area of the receiver, and wherein, when the first bone screw is disposed in the first screw hole, the upper restraint part prevents the first bone screw from being separated from the first screw hole, and when the second bone screw is disposed in the second screw hole, the lower restraint part prevents the second bone screw from being separated from the second screw hole.

* * * * *